United States Patent [19]
Kato et al.

[11] Patent Number: 6,036,842
[45] Date of Patent: Mar. 14, 2000

[54] GAS SENSOR, METHOD FOR CONTROLLING GAS SENSOR, GAS CONCENTRATION CONTROLLER, AND METHOD FOR CONTROLLING GAS CONCENTRATION

[75] Inventors: Nobuhide Kato, Ama-Gun; Noriyuki Ina, Okazaki, both of Japan

[73] Assignee: NGK Insulators, Ltd., Japan

[21] Appl. No.: 08/882,075

[22] Filed: Jun. 25, 1997

[30] Foreign Application Priority Data

Jun. 28, 1996 [JP] Japan .................................. 8-170160

[51] Int. Cl.⁷ .................................................. G01N 27/407
[52] U.S. Cl. .......................... 205/781; 204/425; 204/426; 205/784.5; 205/786.5; 205/788
[58] Field of Search ........................... 204/412, 421–429; 205/780.5, 781, 783.5, 784, 784.5, 785, 786.5, 788

[56] References Cited

U.S. PATENT DOCUMENTS

| 4,857,164 | 8/1989 | Kodachi et al. | 204/406 |
| 4,927,517 | 5/1990 | Mizutani et al. | 204/425 |
| 5,672,811 | 9/1997 | Kato et al. | 204/427 |

FOREIGN PATENT DOCUMENTS

| 0 310 206 A2 | 4/1989 | European Pat. Off. . |
| 0 517 364 A2 | 12/1992 | European Pat. Off. . |
| 0 678 740 A1 | 10/1995 | European Pat. Off. . |
| 2288873 | 11/1995 | United Kingdom . |

OTHER PUBLICATIONS

Japanese Utility Model Publication No. 7–45004; published Oct. 11, 1995; "Oxygen Sensor" (Toyota Motor Corporation).

*Primary Examiner*—T. Tung
*Attorney, Agent, or Firm*—Parkhurst & Wendel, L.L.P.

[57] ABSTRACT

A system is constructed such that a voltage between an inner pumping electrode and a reference electrode is measured to determine a difference between a measured voltage and a reference voltage so that a pumping voltage is controlled by using the differential voltage. Specifically, a comparative amplifier is provided for comparing the reference voltage with the terminal voltage between the reference electrode and the inner pumping electrode, and amplifying the difference therebetween with a predetermined gain to make an output. The system is wired and connected such that the output voltage (differential voltage) from the comparative amplifier is applied, as the pumping voltage supplied to an oxygen pump, between the inner pumping electrode and an outer pumping electrode. The inner pumping electrode is grounded. Accordingly, for example, when the oxygen pump is used, it is possible to effectively avoid the oscillation phenomenon in the feedback control system for the control voltage for the oxygen pump.

19 Claims, 17 Drawing Sheets

FIG.6

| OXYGEN CONCENTRATION | COMPARATIVE EXAMPLE | WORKING EXAMPLE |
|---|---|---|
| 0% | 400mV | 400mV |
| 5% | 310mV | 360mV |
| 20% | 30mV | 250mV |

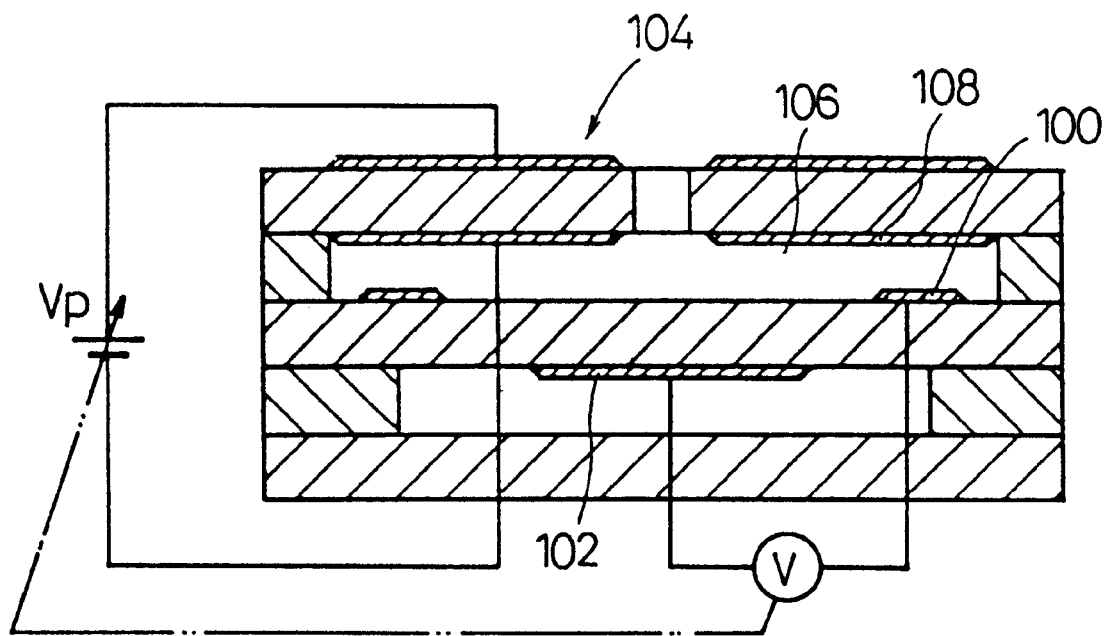
F I G. 12

F I G. 14
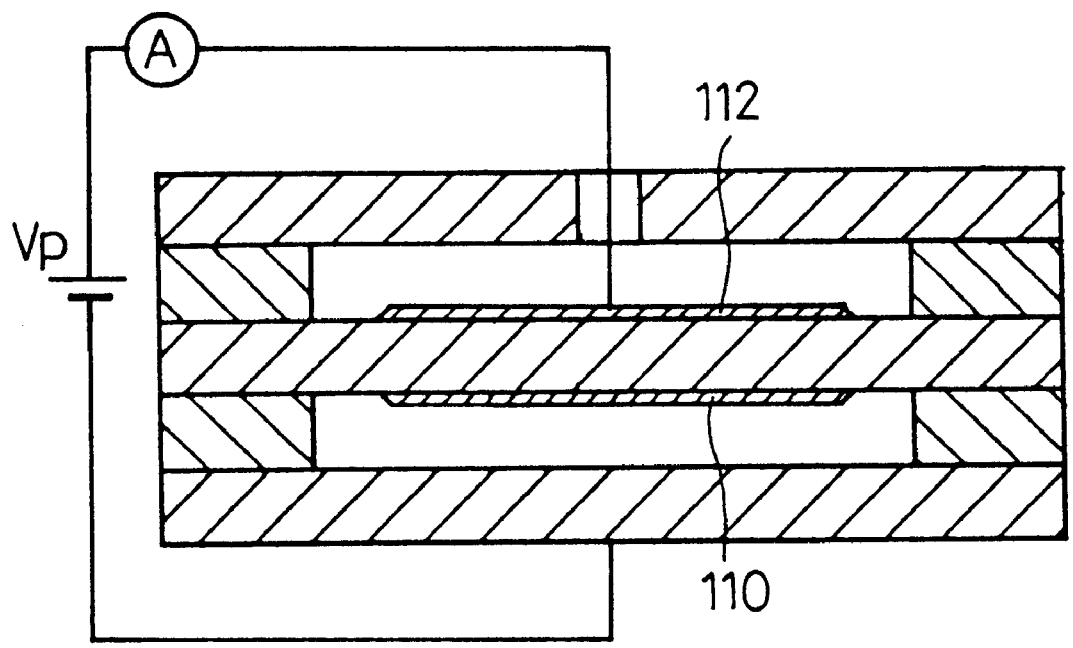

GAS SENSOR, METHOD FOR CONTROLLING GAS SENSOR, GAS CONCENTRATION CONTROLLER, AND METHOD FOR CONTROLLING GAS CONCENTRATION

BACKGROUND OF THE INVENTION

1. Field of the Invention

The present invention relates to a gas sensor, a method for controlling the same, a gas concentration controller, and a method for controlling gas concentration, used to measure oxides such as NO, $NO_2$, $SO_2$, $CO_2$, and $H_2O$ contained in, for example, atmospheric air and exhaust gas discharged from vehicles or automobiles, and inflammable gases such as CO and CnHm.

2. Description of the Related Art

In recent years, exhaust gas, which is discharged from vehicles or automobiles such as gasoline-fueled automobiles and diesel powered automobiles, contains nitrogen oxides (NOx) such as nitrogen monoxide (NO) and nitrogen dioxide ($NO_2$), as well as carbon monoxide (CO), carbon dioxide ($CO_2$), water ($H_2O$), hydrocarbon (HC), hydrogen ($H_2$), oxygen ($O_2$) and so on. In such exhaust gas, about 80% of the entire NOx is occupied by NO, and about 95% of the entire NOx is occupied by NO and $NO_2$.

The three way catalyst, which is used to clean HC, CO, and NOx contained in the exhaust gas, exhibits its maximum cleaning efficiency in the vicinity of the theoretical air fuel ratio (A/F=14.6). If A/F is controlled to be not less than 16, the amount of produced NOx is decreased. However, the cleaning efficiency of the catalyst is lowered, and consequently the amount of discharged NOx is apt to increase.

Recently, in order to effectively utilize fossil fuel and avoid global warming, the market demand increases, for example, in that the discharge amount of $CO_2$ should be suppressed. In order to respond to such a demand, it becomes more necessary to improve the fuel efficiency. In response to such a demand, for example, the lean burn engine and the catalyst for cleaning NOx are being researched. Especially, the need for a NOx sensor increases.

A conventional NOx analyzer has been hitherto known as an instrument for detecting NOx. The conventional NOx analyzer is operated to measure a characteristic inherent in NOx, based on the use of chemical luminous analysis. However, the conventional NOx analyzer is inconvenient in that the instrument itself is extremely large and expensive.

The conventional NOx analyzer requires frequent maintenance because optical parts are used to detect NOx. Further, when the conventional NOx analyzer is used, any sampling operation should be performed for measurement of NOx, wherein it is impossible to directly insert a detecting element itself into a fluid. Therefore, the conventional NOx analyzer is not suitable for analyzing transient phenomena such as those occur in the exhaust gas discharged from an automobile, in which the condition frequently varies.

In order to dissolve the inconveniences as described above, there has been suggested a sensor for measuring a desired gas component in exhaust gas by using a substrate composed of an oxygen ion-conductive solid electrolyte.

The suggested conventional gas sensor is exemplified by an all-range type oxygen sensor as shown in FIG. 12. Further, a gas sensor for measuring NOx is also known, with which a gas (for example, NOx) including bound oxygen is measured by lowering the oxygen concentration in the gas to a constant low level by using an oxygen pump, and then further lowering the oxygen concentration to decompose NOx so that oxygen produced during the decomposition is measured by using an oxygen pump.

For example, the gas sensor shown in FIG. 12 will be explained. In this gas sensor, a direct current voltage to be applied to an oxygen pump 104 is subjected to feedback control so that a voltage of electromotive force generated between a measuring electrode 100 and a reference electrode 102 is maintained to be constant. In general, the feedback control is performed by comparing a comparative voltage as a target with the electromotive force generated between the measuring electrode 100 and the reference electrode 102 by using a comparator, amplifying a difference produced by the comparator to generate an amplified voltage corresponding to the difference from the target value, and applying the amplified voltage to the pump.

However, the conventional gas sensor involves problems concerning the following two point. Firstly, for example, when the gain of the amplifier is set to be excessively large in the gas sensor shown in FIG. 12, the feedback control suffers oscillation (first problem). Secondly, when the measurement gas has a high oxygen concentration, it is impossible to accurately measure the oxygen concentration (second problem).

At first, the first problem will be specifically explained. The first problem is caused by the existence of any geometrical dimension of the measuring electrode 100 and a pumping electrode 108 contacting with an internal space 106. For example, when the oxygen concentration around the measuring electrode 100 is lower than the target value, the feedback control is performed so that the pumping voltage Vp is increased. Accordingly, the pumping voltage Vp is increased, the oxygen in the internal space 106 is pumped out, and the oxygen concentration in the internal space 106 is gradually decreased. However, the decrease in oxygen concentration is transmitted to the measuring electrode 100 in a delayed manner due to the presence of the geometrical dimension described above. As a result, the oxygen concentration in the internal space 106 becomes lower than the target value. The lower oxygen concentration is detected by the measuring electrode 100 after a short delay period, and then the feedback control is performed so that the pumping voltage Vp is decreased.

In this case, the partial pressure of oxygen in the internal space 106 is gradually increased in the same manner as described above. However, a phenomenon occurs due to the geometrical dimension, in which the oxygen concentration in the internal space 106 has been excessively increased when the measuring electrode 100 detects the increase. As a result, the feedback control circuit suffers oscillation.

In order to solve this problem, if the gain of the amplifier is decreased, a state of insufficient control occurs when the oxygen concentration in the measurement gas is increased, because of the following reason. Namely, when the oxygen concentration in the measurement gas is increased, it is necessary to use a large pumping voltage Vp. However, the pumping voltage Vp cannot be increased to a desired valued because of the small gain.

Next, the second problem will be explained. In general, the limiting current type oxygen sensor based on the use of the oxygen pump is exemplified by widely known sensors as shown in FIGS. 13 and 14, in which a constant pumping voltage Vp is applied between an air electrode 110 and an electrode 112 disposed on the side of exhaust gas so that the oxygen concentration is measured based on a value of a current flowing therebetween. Upon the operation of such a sensor, the constant pumping voltage Vp is applied. Therefore, for example, when the oxygen concentration is increased, the amount corresponding to electromotive force is decreased by the amount corresponding to impedance of the oxygen pump. As a result, an oxygen concentration to be substantially controlled is increased. In such a situation, it is impossible to accurately measure the oxygen concentration (the oxygen concentration is higher at Point B than at Point A in a characteristic curve shown in FIG. 15).

On the other hand, Japanese Utility Model Publication No. 7-45004 discloses a system in which a voltage corresponding to a pumping current is generated by using an operational amplifier. The voltage is returned to the operational amplifier via a feedback resistor, and it is supplied to a resistor which is connected to a power source in series. When the pumping current is increased, the voltage generated by the resistor is superimposed and applied to the pump.

This system comprises a circuit as shown in FIG. 16. The output of the operational amplifier OP is returned to an input terminal on a side of an air electrode 110 via the feedback resistor R1 so that the voltage corresponding to the pumping current is generated at an output point A. On the other hand, the output is returned to an input terminal of an electrode 112 disposed on the side of exhaust gas via the resistor R2, and the current is allowed to flow via the resistor r so that an amount of voltage generated in the resistor r is superimposed on a power source voltage $V_E$.

When the resistor connected to the power source in series is appropriately designed, a voltage corresponding (actual pump impedance x pumping current) is superimposed on the pumping voltage Vp so that the operation point is set at any of certain flat portions on limiting current characteristic curves as shown in FIG. 17. Thus the oxygen concentration is measured with a high degree of accuracy.

However, when the oxygen concentration in a measurement gas is increased, the amount corresponding to voltage drop is increased, and it becomes far larger than the amount corresponding to electromotive force. Therefore, it is difficult to operate the gas sensor at an operation point which accurately corresponds to a certain electromotive force.

When the temperature of exhaust gas greatly changes as in the automobile, the sensor is provided with a heater, for which a mechanism for controlling the electric power to be supplied to the heater is provided, in some cases. Even when such a system is adopted, the impedance of the oxygen pump is slightly changed. When the pumping current is increased, a large error occurs in correction for the amount corresponding to voltage drop. As a result, it is difficult to correctly measure the high oxygen concentration.

This problem is most serious especially when the pump is used as an oxygen concentration controller. When the pump is used as an oxygen sensor, even if the oxygen concentration in the measurement gas is increased, the pumping current is increased, and the oxygen concentration in the measurement space is increased from $10^{-10}$ atm to $10^{-3}$ atm, then the change in current based on the change in oxygen concentration is about several % at most, as compared with the increased pumping current. However, when the pump is used as an oxygen concentration controller, the change in oxygen concentration is exactly the large change from $10^{-10}$ atm to $10^{-3}$ atm as it is.

As described above, the conventional gas sensor involves the first problem that the feedback control system suffers oscillation when the voltage applied to the oxygen pump is controlled on the basis of the electromotive force between the measuring electrode and the reference electrode, and the second problem that it is impossible to accurately absorb the error of the amount corresponding to the voltage drop resulting from the impedance of the oxygen pump.

SUMMARY OF THE INVENTION

The present invention has been made taking the foregoing problems into consideration, an object of which is to provide a gas sensor, a method for controlling a gas sensor, a gas concentration controller, and a method for controlling gas concentration which make it possible to effectively avoid the oscillation phenomenon of a feedback control system for a control voltage supplied to an oxygen pump, for example, when the oxygen pump is used.

Another object of the present invention is to provide a gas sensor, a method for controlling a gas sensor, a gas concentration controller, and a method for controlling gas concentration which make it possible to absorb the error in the amount corresponding to voltage drop resulting from the impedance of the oxygen pump so that the oxygen concentration can be accurately detected.

In order to achieve the objects described above, the present invention provides a gas sensor comprising a first space surrounded by substrates composed of solid electrolytes, for introducing a measurement gas thereinto; a gas-pumping means including inner and outer electrodes formed inside and outside the first space surrounded by the substrates respectively, the substrate interposed by the both electrodes, and a pumping power source for applying, between the both electrodes, a control voltage for pumping out a predetermined gas component; a second space surrounded by substrates composed of solid electrolytes, for introducing a reference gas thereinto; a measuring means for measuring a terminal voltage between a reference electrode formed on the substrate and disposed on a side of the second space and the inner electrode of the gas-pumping means; and a control voltage-adjusting means for adjusting a level of the control voltage on the basis of the terminal voltage.

According to the present invention, at first, the measurement gas is introduced into the first space. At this time, the measuring means is operated to measure the terminal voltage between the inner electrode of the gas-pumping means and the reference electrode formed on the side of the second space. The measured voltage is supplied to the control voltage-adjusting means. The control voltage-adjusting means adjusts the level of the control voltage to be supplied to the gas-pumping means, on the basis of the measured voltage. The gas-pumping means pumps out an amount of the predetermined gas component contained in the measurement gas introduced into the first space, the amount corresponding to the level of the control voltage. The supply of the level-adjusted control voltage to the gas-pumping means allows the concentration of the predetermined gas component in the first space to be subjected to feedback control so that a predetermined level is achieved.

In the present invention, the measured voltage measured by the measuring means to be utilized for adjusting the level of the control voltage is the terminal voltage between the inner electrode of the gas-pumping means and the reference electrode disposed in the second space. Accordingly, when the amount of the predetermined gas component pumped out by the gas-pumping means is changed, and the concentration of the gas component is changed in the first space, then the terminal voltage between the inner electrode of the gas-pumping means and the reference electrode is changed without any time delay. Therefore, the oscillation phenomenon in the feedback control disappears.

In one embodiment of the present invention, it is preferable that the control voltage-adjusting means is provided with a comparing means for determining a deviation between the voltage of electromotive force and a comparative voltage, and the level of the control voltage is adjusted on the basis of the deviation obtained by the comparing means. In this embodiment, the control voltage is subjected to feedback control so that the terminal voltage converges to the comparative voltage.

In another embodiment of the present invention constructed as described above, it is preferable that the gas sensor further comprises a current-detecting means for detecting a current flowing through the gas-pumping means when the gas component is pumped out by the gas-pumping means, and a comparative voltage-adjusting means for adjusting a level of the comparative voltage on the basis of a value of the current detected by the current-detecting means.

In general, the current flows through the gas pump when the predetermined gas component is pumped out by the gas-pumping means. Therefore, the amount corresponding to voltage drop resulting from the impedance of the gas pump appears as an error for the level adjustment for the control voltage. However, according to the present invention, the current flowing through the gas-pumping means is detected, and the value of the detected current is reflected in the comparative voltage. Therefore, the error is effectively absorbed, and the oscillation phenomenon does not occur in the feedback control for the gas-pumping means, making it possible to accurately perform the feedback control. Thus the concentration of the predetermined gas component contained in the measurement gas introduced into the first space can be detected with a high degree of accuracy.

In still another embodiment of the present invention as described above, it is preferable that a gas diffusion rate-determining section for giving a predetermined diffusion resistance to the measurement gas is provided at a passage for introducing the measurement gas into the first space. In still another embodiment, it is preferable that the gas sensor further comprises a third space for introducing the measurement gas in the first space thereinto; a second gas diffusion-rate determining section provided at a passage for introducing the measurement gas into the third space, for giving a predetermined diffusion resistance to the measurement gas; a measurement gas-decomposing means disposed in the third space, for decomposing and degrading the predetermined gas component in the measurement gas; and a gas component-detecting means for detecting the predetermined gas component decomposed and degraded by the measurement gas-decomposing means. Alternatively, it is preferable that the gas sensor further comprises a gas component supply means for feeding the predetermined gas component to the third space; and a gas component-detecting means for detecting the gas component fed by the gas component supply means. In this embodiment, the amount of the predetermined gas component contained in the measurement gas can be effectively controlled, making it possible to measure, for example, the amount of oxides or inflammable gases contained in the measurement gas with a high degree of accuracy.

According to another aspect of the present invention, there is provided a method for controlling a gas sensor, the gas sensor comprising a first space surrounded by substrates composed of solid electrolytes, for introducing a measurement gas thereinto; a gas-pumping means including inner and outer electrodes formed inside and outside the first space surrounded by the substrates respectively, the substrate interposed by the both electrodes, and a pumping power source for applying, between the both electrodes, a control voltage for pumping out a predetermined gas component; a second space surrounded by substrates composed of solid electrolytes, for introducing a reference gas thereinto; and a reference electrode formed on the substrate and disposed on a side of the second space; the method comprising the steps of measuring a terminal voltage between the reference electrode and the inner electrode of the gas-pumping means, and adjusting a level of the control voltage on the basis of the voltage.

According to the present invention, at first, the measurement gas is introduced into the first space. At this time, the terminal voltage between the inner electrode of the gas-pumping means and the reference electrode formed on the side of the second space is measured. The level of the control voltage to be supplied to the gas-pumping means is adjusted on the basis of the measured voltage. The gas-pumping means pumps out an amount of the predetermined gas component contained in the measurement gas introduced into the first space, the amount corresponding to the level of the control voltage. The supply of the level-adjusted control voltage to the gas-pumping means allows the concentration of the predetermined gas component in the first space to be subjected to feedback control so that a predetermined level is achieved.

In the present invention, the measured voltage to be utilized for adjusting the level of the control voltage is the terminal voltage between the inner electrode of the gas-pumping means and the reference electrode disposed in the second space. Accordingly, when the amount of the predetermined gas component pumped out by the gas-pumping means is changed, and the concentration of the gas component is changed in the first space, then the terminal voltage between the inner electrode of the gas-pumping means and the reference electrode is changed without any time delay. Therefore, the oscillation phenomenon in the feedback control disappears.

In one embodiment of the present invention, it is preferable that the control voltage is adjusted by determining a deviation between the voltage of electromotive force and a comparative voltage, and adjusting the level of the control voltage on the basis of the obtained deviation. In this embodiment, the control voltage is subjected to feedback control so that the measured voltage converges to the comparative voltage.

In another embodiment of the method for controlling the gas sensor, it is preferable that a current flowing through the gas-pumping means is detected when the gas component is pumped out by the gas-pumping means, and a level of the comparative voltage is adjusted on the basis of a value of the detected current.

In general, the current flows through the gas pump when the predetermined gas component is pumped out by the gas-pumping means. Therefore, the amount corresponding to voltage drop resulting from the impedance of the gas pump appears as an error for the level adjustment for the control voltage. However, according to the present invention, the current flowing through the gas-pumping means is detected, and the value of the detected current is reflected in the comparative voltage. Therefore, the error is effectively absorbed, and the oscillation phenomenon does not occur in the feedback control for the gas-pumping means, making it possible to accurately perform the feedback control. Thus the concentration of the predetermined gas component contained in the measurement gas introduced into the first space can be detected with a high degree of accuracy.

In still another embodiment of the method for controlling the gas sensor according to the present invention, it is preferable that a gas diffusion rate-determining section for giving a predetermined diffusion resistance to the measurement gas is provided at a passage for introducing the measurement gas into the first space. In still another embodiment, it is preferable that the gas sensor further comprises a third space for introducing the measurement gas in the first space thereinto; a second gas diffusion-rate determining section provided at a passage for introducing the measurement gas into the third space, for giving a predetermined diffusion resistance to the measurement gas; a measurement gas-decomposing means disposed in the third space, for decomposing and degrading the predetermined gas component in the measurement gas; and a gas component-detecting means for detecting the predetermined gas component decomposed and degraded by the measurement gas-decomposing means. Alternatively, it is preferable that the gas sensor further comprises a gas component supply means for feeding the predetermined gas component to the third space; and a gas component-detecting means for detecting the gas component fed by the gas component supply means. In this embodiment, the amount of the predetermined gas component contained in the measurement gas can be effectively controlled, making it possible to measure, for example, the amount of oxides or inflammable gases contained in the measurement gas with a high degree of accuracy.

According to still another aspect of the present invention, there is provided a gas concentration controller comprising a first space surrounded by substrates composed of solid electrolytes, for introducing a measurement gas thereinto; a gas diffusion rate-determining section provided at a passage for introducing the measurement gas into the first space, for giving a predetermined diffusion resistance to the measurement gas; a gas-pumping means including inner and outer electrodes formed inside and outside the first space surrounded by the substrates respectively, the substrate interposed by the both electrodes, and a pumping power source for applying, between the both electrodes, a control voltage for pumping out a predetermined gas component; a second space surrounded by substrates composed of solid electrolytes, for introducing a reference gas thereinto; a measuring means for measuring a terminal voltage between a reference electrode formed on the substrate and disposed on a side of the second space and the inner electrode of the gas-pumping means; and a control voltage-adjusting means for adjusting a level of the control voltage on the basis of the terminal voltage.

According to the present invention, at first, the measurement gas is introduced into the first space via the gas diffusion rate-determining section. At this time, the measuring means is operated to measure the terminal voltage between the inner electrode of the gas-pumping means and the reference electrode formed on the side of the second space. The measured voltage is supplied to the control voltage-adjusting means. The control voltage-adjusting means adjusts the level of the control voltage to be supplied to the gas-pumping means, on the basis of the measured voltage. The gas-pumping means pumps out an amount of the predetermined gas component contained in the measurement gas introduced into the first space, the amount corresponding to the level of the control voltage. The supply of the level-adjusted control voltage to the gas-pumping means allows the concentration of the predetermined gas component in the first space to be subjected to feedback control so that a predetermined level is achieved.

In the present invention, the measured voltage measured by the measuring means to be utilized for adjusting the level of the control voltage is the terminal voltage between the inner electrode of the gas-pumping means and the reference electrode disposed in the second space. Accordingly, when the amount of the predetermined gas component pumped out by the gas-pumping means is changed, and the concentration of the gas component is changed in the first space, then the terminal voltage between the inner electrode of the gas-pumping means and the reference electrode is changed without any time delay. Therefore, the oscillation phenomenon in the feedback control disappears.

In one embodiment of the present invention, it is preferable that the control voltage-adjusting means is provided with a comparing means for determining a deviation between the voltage of electromotive force and a comparative voltage, and the level of the control voltage is adjusted on the basis of the deviation obtained by the comparing means. In this embodiment, the control voltage is subjected to feedback control so that the terminal voltage converges to the comparative voltage.

In another embodiment of the present invention constructed as described above, it is preferable that the gas concentration controller further comprises a current-detecting means for detecting a current flowing through the gas-pumping means when the gas component is pumped out by the gas-pumping means, and a comparative voltage-adjusting means for adjusting a level of the comparative voltage on the basis of a value of the current detected by the current-detecting means.

In general, the current flows through the gas pump when the predetermined gas component is pumped out by the gas-pumping means. Therefore, the amount corresponding to voltage drop resulting from the impedance of the gas pump appears as an error for the level adjustment for the control voltage. However, according to the present invention, the current flowing through the gas-pumping means is detected, and the value of the detected current is reflected in the comparative voltage. Therefore, the error is effectively absorbed, and the oscillation phenomenon does not occur in the feedback control for the gas-pumping means, making it possible to accurately perform the feedback control. Thus the concentration of the predetermined gas component contained in the measurement gas introduced into the first space can be detected with a high degree of accuracy.

According to still another aspect of the present invention, there is provided a method for controlling gas concentration, comprising the steps of introducing a measurement gas into a first space surrounded by substrates composed of solid electrolytes; applying a control voltage for pumping out a predetermined gas component between inner and outer electrodes formed inside and outside the first space surrounded by the substrates respectively; introducing a reference gas into a second space surrounded by substrates composed of solid electrolytes; measuring a terminal voltage between a reference electrode formed on the substrate and disposed on a side of the second space and the inner electrode; and adjusting a level of the control voltage on the basis of the terminal voltage.

In the present invention, the measured voltage measured by the measuring means to be utilized for adjusting the level of the control voltage is the terminal voltage between the inner electrode of the gas-pumping means and the reference electrode disposed in the second space. Accordingly, when the amount of the predetermined gas component pumped out by the gas-pumping means is changed, and the concentration of the gas component is changed in the first space, then the terminal voltage between the inner electrode of the gas-pumping means and the reference electrode is changed without any time delay. Therefore, the oscillation phenomenon in the feedback control disappears.

In one embodiment of the present invention, it is preferable that the control voltage is adjusted by determining a deviation between the voltage of electromotive force and a comparative voltage, and adjusting the level of the control voltage on the basis of the obtained deviation. In this embodiment, the control voltage is subjected to feedback control so that the measured voltage converges to the comparative voltage.

In another embodiment of the method for controlling the gas concentration, it is preferable that a current flowing through the substrate is detected when the predetermined gas component is pumped out, and a level of the comparative voltage is adjusted on the basis of a value of the detected current.

In general, the current flows through the substrate when the predetermined gas component is pumped out. Therefore, the amount corresponding to voltage drop resulting from the impedance of the substrate appears as an error for the level adjustment for the control voltage. However, according to the present invention, the current flowing through the substrate is detected, and the value of the detected current is reflected in the comparative voltage. Therefore, the error is effectively absorbed, and the oscillation phenomenon does not occur in the feedback control for the control voltage, making it possible to accurately perform the feedback control. Thus the concentration of the predetermined gas component contained in the measurement gas introduced into the first space can be detected with a high degree of accuracy.

In still another embodiment, it is preferable that a predetermined diffusion resistance is given to the measurement gas when the measurement gas is introduced into the first space.

The above and other objects, features and advantages of the present invention will become more apparent from the following description when taken in conjunction with the accompanying drawings in which a preferred embodiment of the present invention is shown by way of illustrative example.

DESCRIPTION OF THE DRAWINGS

FIG. 6 shows a table for comparing actual amounts corresponding to the electromotive force obtained in a comparative example with those obtained in a working example, in which it is intended to correct and control the amount corresponding to the electromotive force to be 400 mV when the oxygen concentration in the measurement gas is changed.

FIG. 12 shows an arrangement illustrating a conventional all-range type oxygen gas sensor.

FIG. 14 shows an arrangement illustrating a limiting current type oxygen sensor (No. 2) based on the use of the conventional oxygen pump.

DESCRIPTION OF THE PREFERRED EMBODIMENTS

Explanation will be made below with reference to FIGS. 1 to 11 for two illustrative embodiments in which the gas sensor according to the present invention is applied to a gas sensor for measuring oxides such as NO, $NO_2$, $SO_2$, $CO_2$, and $H_2O$ contained in, for example, atmospheric air and exhaust gas discharged from vehicles or automobiles, and inflammable gases such as CO and CnHm (hereinafter simply referred to as "gas sensor according to the first embodiment" and "gas sensor according to the second embodiment" respectively).

Figure 1:
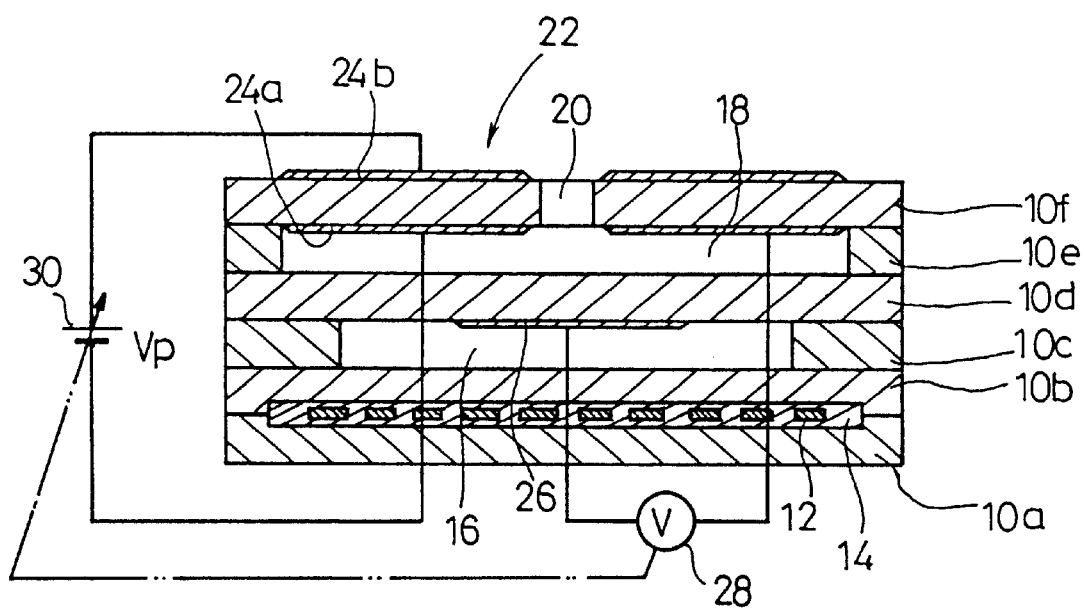
FIG. 1 shows a schematic arrangement of a first illustrative embodiment in which the gas sensor according to the present invention is applied to a gas sensor for measuring oxides such as NO, $NO_2$, $SO_2$, $CO_2$, and $H_2O$ contained in, for example, atmospheric air and exhaust gas discharged from vehicles or automobiles, and inflammable gases such as CO and CnHm (hereinafter simply referred to as "gas sensor according to the first embodiment").
Figure 2:
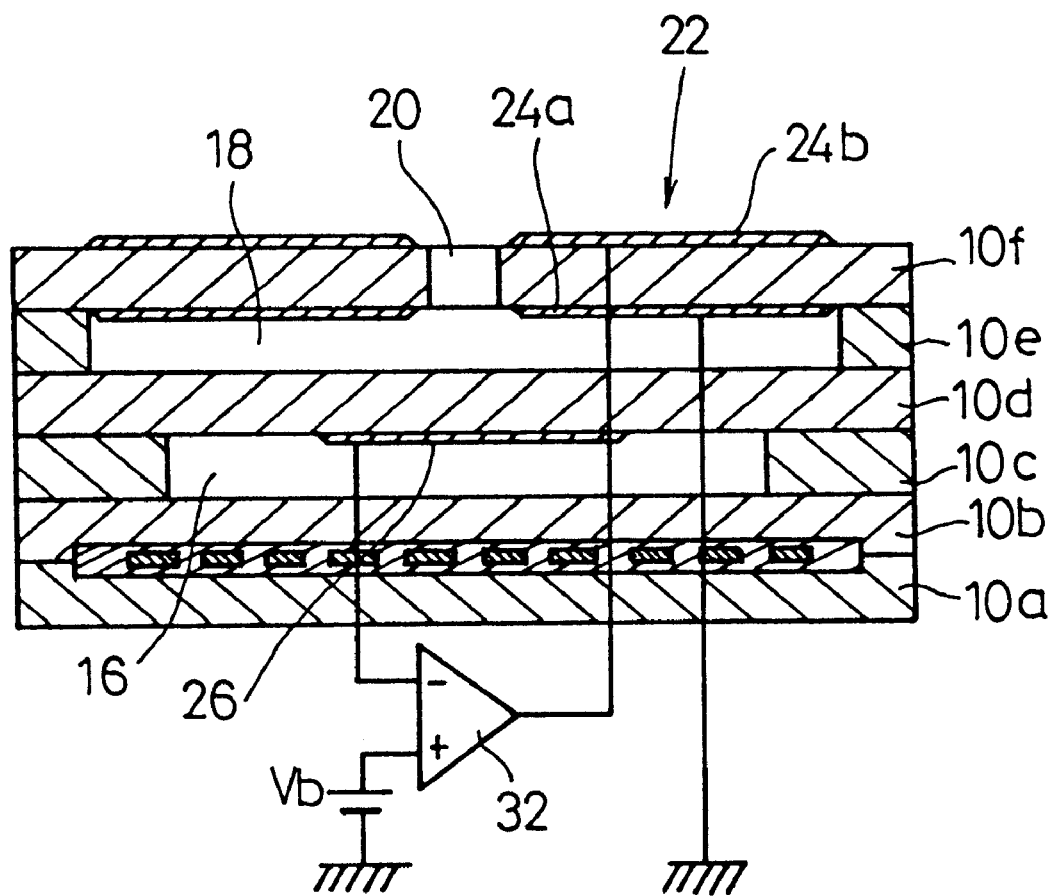
FIG. 2 shows a specified arrangement of the gas sensor according to the first embodiment.

At first, as shown in FIGS. 1 and 2, the gas sensor according to the first embodiment comprises, for example, six stacked solid electrolyte layers 10a to 10f composed of ceramics based on the use of oxygen ion-conductive solid electrolytes such as $ZrO_2$. First and second layers from the bottom are designated as first and second substrate layers 10a, 10b respectively. Third and fifth layers from the bottom are designated as first and second spacer layers 10c, 10e respectively. Fourth and sixth layers from the bottom are designated as first and second solid electrolyte layers 10d, 10f respectively.

Specifically, the first spacer layer 10c is stacked on the second substrate layer 10b. The first solid electrolyte layer 10d, the second spacer layer 10e, and the second solid electrolyte layer 10f are successively stacked on the first spacer layer 10c. A heater 12 for enhancing the oxygen ion conductivity is embedded through an insulative film 14 between the first and second substrate layers 10a, 10b.

A space (reference gas-introducing space) 16, into which a reference gas such as atmospheric air to be used as a reference for measuring oxides is introduced, is formed between the second substrate layer 10b and the first solid electrolyte layer 10d, the space 16 being comparted by a lower surface of the first solid electrolyte layer 10d, an upper surface of the second substrate layer 10b, and side surfaces of the first spacer layer 10c.

A space (gas-introducing space) 18, into which a measurement gas is introduced, is formed between the first and second solid electrolyte layers 10d, 10f, the space 18 being comparted by a lower surface of the second solid electrolyte layer 10f, an upper surface of the first electrolyte layer 10d, and side surfaces of the second spacer layer 10e. A diffusion rate-determining section 20, which communicates with the gas-introducing space 18, is formed through the uppermost second solid electrolyte layer 10f. The diffusion rate-determining section 20 is provided for giving a predetermined diffusion resistance to the measurement gas to be introduced into the gas-introducing space 18. The diffusion-rate determining section 20 can be formed as a passage composed of, for example, a porous material, or a small hole having a predetermined cross-sectional area so that the measurement gas may be introduced.

A first electrode (inner pumping electrode 24a) for constructing an oxygen pump 22 as described later on is formed on a portion of the lower surface of the second solid electrolyte layer 10f for forming the gas-introducing space 18. A second electrode (outer pumping electrode 24b) for constructing the oxygen pump 22 is formed on the upper surface of the second solid electrolyte layer 10f.

A reference electrode 26 for measuring the partial pressure of oxygen contained in the measurement gas is formed on a portion of the lower surface of the first solid electrolyte layer 10d for forming the reference gas-introducing space 16.

In this arrangement, an electromotive force of an oxygen concentration cell is generated on the basis of a difference between a partial pressure of oxygen in the atmospheric air introduced into the reference gas-introducing space 16 and a partial pressure of oxygen in the measurement gas introduced into the gas-introducing space 18. The electromotive force is represented by an electric potential difference V between the reference gas-introducing space 16 and the gas-introducing space 18. The electric potential difference V can be determined in accordance with the following Nernst's equation.

$$V = RT/4F \cdot \ln(P_1(O_2)/P_0(O_2))$$

R: gas constant;
T: absolute temperature;
F: Faraday constant;
$P_1(O_2)$: partial pressure of oxygen in the gas-introducing space;
$P_0(O_2)$: partial pressure of oxygen in the reference gas.

Therefore, the partial pressure of oxygen in the gas-introducing space 18 can be detected by measuring the electric potential difference V generated on the basis of the Nernst's equation, by using a potentiometer 28.

The inner pumping electrode 24a and the outer pumping electrode 24b, which are formed on the inner and outer surfaces of the second solid electrolyte layer 10f respectively, construct the oxygen pump 22 for setting the partial pressure of oxygen in the measurement gas introduced into the gas-introducing space 18 to have a predetermined value. Namely, the solid electrolyte layer, which is composed of a material such as $ZrO_2$ provided with the oxygen ion conductivity, functions as a pump for pumping out oxygen upon application of a voltage. The both pumping electrodes 24a, 24b construct a voltage-applying means for allowing the solid electrolyte layer to perform the pumping operation.

In general, a pumping voltage Vp, which is set on the basis of the electric potential difference V detected by the potentiometer 28, is applied between the inner pumping electrode 24a and the outer pumping electrode 24b by the aid of a variable power source 30. Oxygen is pumped out from or pumped in into the gas-introducing space 18 by the oxygen pump 22 in accordance with application of the pumping voltage Vp. Accordingly, the partial pressure of oxygen in the gas-introducing space 18 is set to have a predetermined value.

The gas sensor according to the first embodiment is arranged such that the voltage between the inner pumping electrode 24a and the reference electrode 26 is measured to determine a difference between the measured voltage and the reference voltage so that the pumping voltage Vp is controlled on the basis of the determined difference in voltage or differential voltage.

Specifically, as shown in FIG. 2, the gas sensor according to the first embodiment is wired and connected as follows. Namely, the gas sensor is provided with a comparative amplifier 32 for comparing the reference voltage Vb with the terminal voltage between the reference electrode 26 and the inner pumping electrode 24 to obtain an amount corresponding to a difference therebetween, and amplifying the amount corresponding to the difference with a predetermined gain to make an output. The output voltage (differential voltage) from the comparative amplifier 32 is applied, as the pumping voltage Vp supplied to the oxygen pump 22, between the inner pumping electrode 24a and the outer pumping electrode 24b. In this embodiment, the inner pumping electrode 24a is grounded.

Next, the operation of the gas pump according to the first embodiment will be explained. At first, the measurement gas is introduced into the gas-introducing space 18 via the diffusion rate-determining section 20. At this time, the terminal voltage, which is obtained between the inner pumping electrode 24a of the oxygen pump 22 and the reference electrode 26 formed on the side of the reference gas-introducing space 16, is applied, for example, to an inverting terminal of the comparative amplifier 32. The comparative amplifier 32 determines the difference between the terminal voltage supplied to the inverting terminal and the reference voltage Vb supplied to a non-inverting terminal. A pumping voltage (output voltage) Vp, which is obtained by amplifying the difference with a predetermined gain, is outputted from an output terminal of the comparative amplifier 32. The output voltage Vp is applied to the outer pumping electrode 24b of the oxygen pump 22. However, in this embodiment, the inner pumping electrode 24a has a ground electric potential (0 V). Consequently, the voltage between the both electrodes of the oxygen pump 22 is equivalent to the output voltage Vp from the comparative amplifier 32. Therefore, the oxygen pump 22 pumps out or pumps in oxygen contained in the measurement gas introduced into the gas-introducing space 18 in an amount corresponding to the level of the output voltage Vp. The oxygen concentration in the gas-introducing space 18 is subjected to feedback control to achieve a predetermined level by repeating the series of operations described above.

In this embodiment, the terminal voltage (measured voltage) to be applied to the inverting terminal of the comparative amplifier 32 is the terminal voltage between the inner pumping electrode 24a of the oxygen pump 22 and the reference electrode 26 disposed in the reference gas-introducing space 16. Therefore, when the amount of oxygen pumped out by the oxygen pump 22 is changed, and the oxygen concentration in the gas-introducing space 18 is changed, then the terminal voltage between the inner pumping electrode 24a of the oxygen pump 22 and the reference electrode 26 is changed without any time delay (the terminal voltage is changed in real-time). Accordingly, the oscillation phenomenon in the feedback control can be effectively suppressed.

In the feedback control system, the pumping voltage Vp (output voltage) is subjected to feedback control so that the terminal voltage between the inner pumping electrode 24a and the reference electrode 26 converges to the same level as that of the reference voltage Vb.

Next, a modified embodiment of the gas sensor according to the first embodiment will be explained with reference to FIG. 3. Components or parts corresponding to those shown in FIG. 1 are designated by the same reference numerals, duplicate explanation of which will be omitted.

Figure 3:
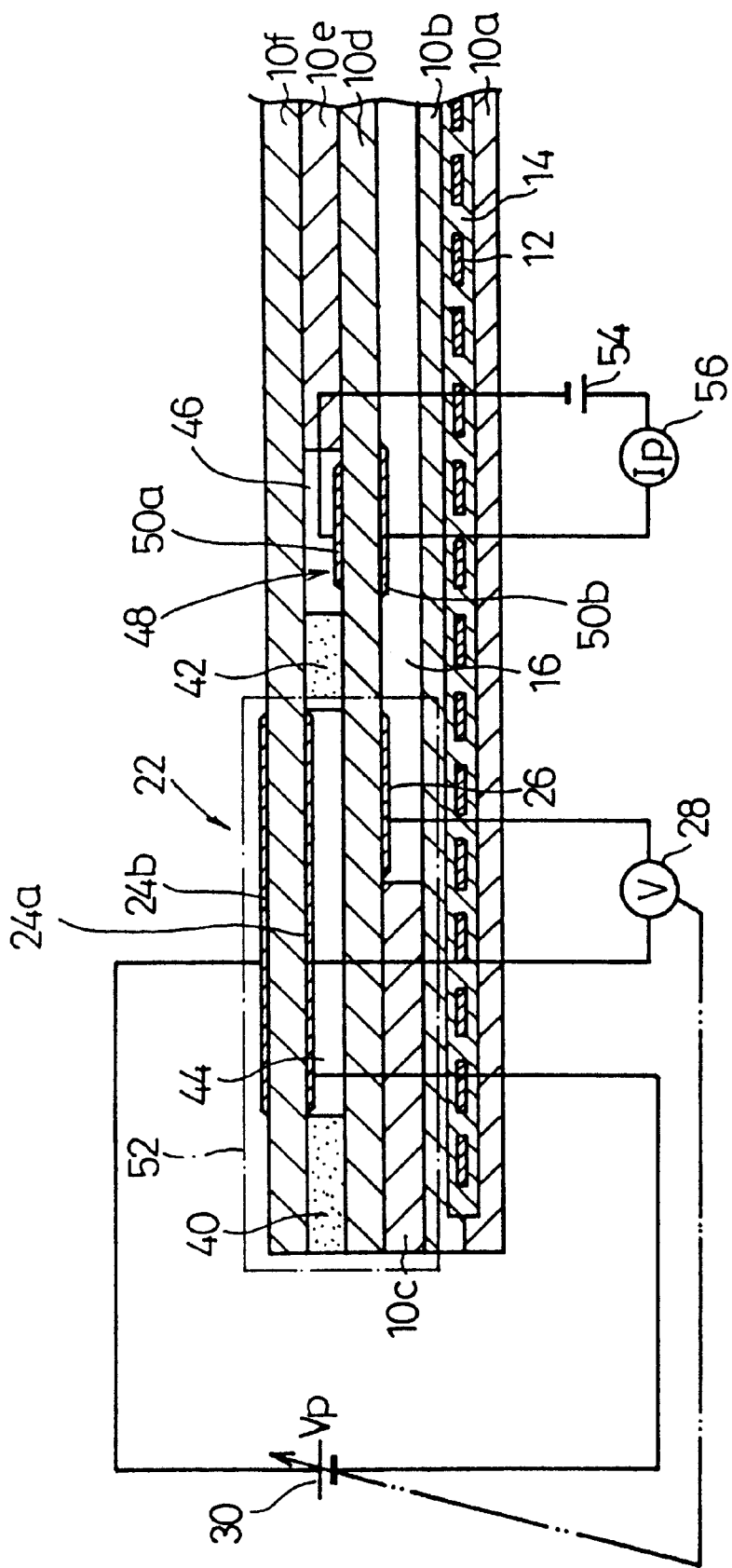
FIG. 3 shows a schematic arrangement of a modified embodiment of the gas sensor according to the first embodiment.

As shown in FIG. 3, the gas sensor according to the modified embodiment is substantially the same as the gas sensor according to the first embodiment in that the gas sensor comprises, for example, six stacked solid electrolyte layers 10a to 10f composed of ceramics based on the use of oxygen ion-conductive solid electrolytes such as $ZrO_2$, and the six solid electrolyte layers 10a to 10f are formed to have a lengthy plate-shaped configuration respectively. However, the former is different from the latter in that a second spacer layer 10e is interposed between the first and second solid electrolyte layers 10d, 10f, and first and second diffusion rate-determining sections 40, 42 are interposed between the first and second solid electrolyte layers 10d, 10f.

A first chamber 44 for adjusting the partial pressure of oxygen in a measurement gas is formed and comparted by a lower surface of the second solid electrolyte layer 10f, side surfaces of the first and second diffusion rate-determining sections 40, 42, and an upper surface of the first solid electrolyte layer 10d. A second chamber 46 for measuring oxides, for example, nitrogen oxides (NOx) in the measurement gas is formed and comparted by a lower surface of the second solid electrolyte layer 10f, a side surface of the second diffusion rate-determining section 42, side surfaces of the second spacer layer 10e, and an upper surface of the first solid electrolyte layer 10d. The first chamber 44 communicates with the second chamber 46 through the second diffusion rate-determining section 42.

A first electrode (upper pumping electrode 50a) for constructing a second oxygen pump 48 as described later on is formed on a portion of the upper surface of the first solid electrolyte layer 10d for forming the second chamber 46. A second electrode (lower pumping electrode 50b) for constructing the second oxygen pump 48 is formed on a portion of the first solid electrolyte layer 10d for forming the reference gas-introducing space 16, the portion being different from the portion for the reference electrode 26.

The first and second diffusion-rate determining sections 40, 42 give predetermined diffusion resistances to the measurement gas to be introduced into the first and second chambers 44, 46 respectively. Each of the first and second diffusion-rate determining sections 40, 42 can be formed as a passage composed of, for example, a porous material, or a small hole having a predetermined cross-sectional area so that the measurement gas may be introduced.

In the gas sensor according to this embodiment, the pumping voltage Vp, which is set on the basis of the electric potential difference detected by the potentiometer 28, is applied between the inner pumping electrode 24a and the outer pumping electrode 24b provided for the first chamber 44, by the aid of the variable power source 30, in the same manner as described above. Oxygen is pumped out from or pumped in into the first chamber 44 by the oxygen pump 22 in accordance with application of the pumping voltage Vp. Accordingly, the partial pressure of oxygen in the first chamber 44 is set to have a predetermined value. Namely, the gas sensor includes an oxygen concentration controller 52 which is constructed by the first chamber 44, the oxygen pump 22, the reference electrode 26, and the reference gas-introducing space 16. Substantial operation for measuring nitrogen oxides is performed in the second chamber 46.

Brief explanation will be made below for the principle of measurement performed by the gas sensor according to the modified embodiment. The pumping voltage Vp is applied by using the oxygen pump 22 of the oxygen concentration controller 52 so that the oxygen concentration in the first chamber 44 is in a degree to prevent NOx from decomposition, for example, at $10^{-7}$ atm. The purpose to prevent NOx from decomposition at $10^{-7}$ atm is achieved by using a material having low NOx reducibility, for example, an alloy of Au and Pt for the inner pumping electrode 24a.

The oxygen concentration in the first chamber 44 is detected on the basis of the terminal voltage between the inner pumping electrode 24a of the oxygen pump 22 and the reference electrode 26, in the same manner as performed in the gas sensor according to the first embodiment described above. The pumping voltage Vp is controlled and applied to the oxygen pump 22 so that the terminal voltage approaches the reference voltage Vb (see FIG. 2), namely, the oxygen concentration in the first chamber 44 is approximately zero.

Accordingly, nitrogen monoxide (NO) remains in the first chamber 44. NO remained in the first chamber 44 passes through the second diffusion rate-determining section 42, and it flows into the next second chamber 46. In the second chamber 46, introduced NO is decomposed into N and O, and the concentration of oxygen O is measured to indirectly determine the concentration of NO. The purpose to cause decomposition of NO is achieved by using a material having NOx reducibility, for example, Rh and Pt for the upper pumping electrode 50a.

The measurement of the oxygen O is performed by measuring the current flowing between the upper pumping electrode 50a and the lower pumping electrode 50b. Specifically, a pumping power source 54 is connected between the lower pumping electrode 50b and the upper pumping electrode 50a so that the current flows in a direction to pump out oxygen $O_2$ from the second chamber 46. During this process, when no oxygen exists in the second chamber 46, migration of oxygen (oxygen pumping out) is not performed between the both electrodes 50a, 50b. Therefore, no current flows between the both electrodes 50a, 50b. When oxygen exists in the second chamber 46, the current flows between the both electrodes 50a, 50b in accordance with the pumping out operation for oxygen. Therefore, the oxygen concentration in the second chamber 46 can be measured by inserting and connecting an ammeter 56 to the pumping power source 54 in series to measure a current value thereof. The current value is proportional to the amount of pumped out oxygen. Accordingly, the amount of NO can be determined from the current value. Accordingly, $NO_2$ can be simultaneously measured equivalently.

Namely, the gas sensor according to the modified embodiment is operated as follows. The oxygen concentration in the measurement gas is made to have a low constant value in the first chamber 44. Bound oxygen is decomposed by the aid of the catalyst or electrolysis in the second chamber 46. Oxygen produced during the decomposition is pumped out by using the second oxygen pump 48. The current, which flows during the pumping out operation, is measured. Thus the concentration of the gas component containing bound oxygen is measured.

When NOx is measured as the gas component containing bound oxygen, it is preferable to decompose NOx by the aid of the catalyst in the second chamber 46. When $H_2O$ and $CO_2$ are measured, it is preferable to perform the operation by the aid of the electrolysis.

When an inflammable gas component such as HC is measured, the operation is performed as follows. At first, the pumping voltage is applied so that the oxygen concentration in the first chamber 44 is at a level, for example, $10^{-15}$ atm at which the inflammable gas component does not burn. The pumping power source is connected in a direction to pump in oxygen into the second chamber 46 so that the inflammable gas component is allowed to burn. During this process, the amount of the inflammable gas can be determined by measuring the amount of oxygen required for the inflammable gas component to burn, i.e., the pumping current.

The gas sensor according to the modified embodiment is constructed in the same manner as the gas sensor according to the first embodiment as follows. Namely, the voltage between the inner pumping electrode 24a and the reference electrode 26 of the oxygen concentration controller 52 is measured to determine a difference between the measured voltage and the reference voltage Vp. The pumping voltage Vp is controlled by using the differential voltage.

Figure 4:
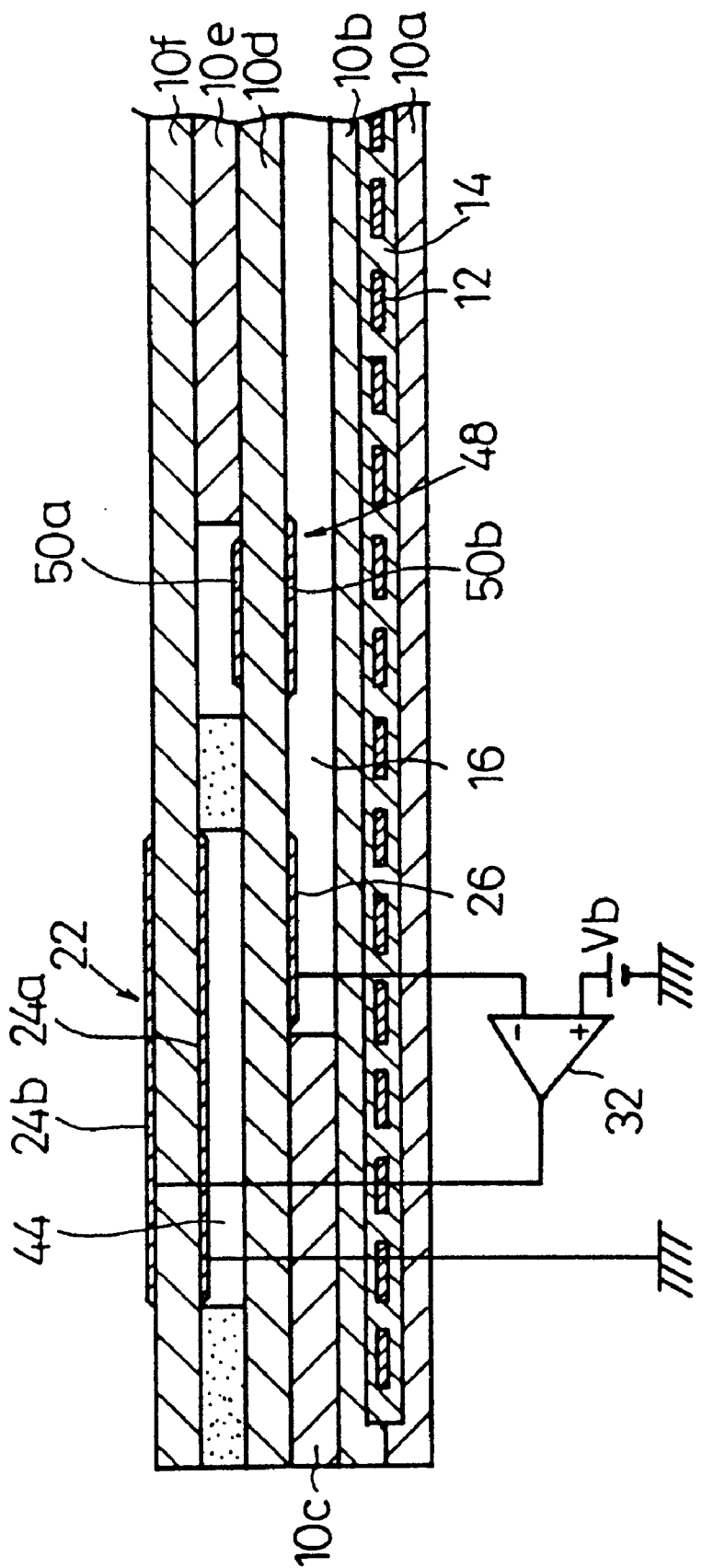
FIG. 4 shows a specified arrangement of the modified embodiment of the gas sensor according to the first embodiment.

Specifically, the gas sensor according to the modified embodiment is wired and connected as shown in FIG. 4, comprising a comparative amplifier 32 for comparing the reference voltage Vb with the terminal voltage between the reference electrode 26 and the inner pumping electrode 24a, and amplifying a different therebetween with a predetermined gain to make an output. The output voltage (differential voltage) from the comparative amplifier 32 is applied, as the pumping voltage Vp supplied to the oxygen pump 22, between the inner pumping electrode 24a and the outer pumping electrode 24b. In this embodiment, the inner pumping electrode 24a is grounded as well.

In the modified embodiment, the terminal voltage (measured voltage), which is applied to the inverting terminal of the comparative amplifier 32, is the terminal voltage between the inner pumping electrode 24a of the oxygen pump 22 and the reference electrode 26 in the reference gas-introducing space 16. Therefore, the change in oxygen concentration in the first chamber 44 appears without any time delay as the change in terminal voltage between the inner pumping electrode 24a of the oxygen pump 22 and the reference electrode 26. Accordingly, it is possible to effectively suppress the oscillation phenomenon in the feedback control.

Figure 5:
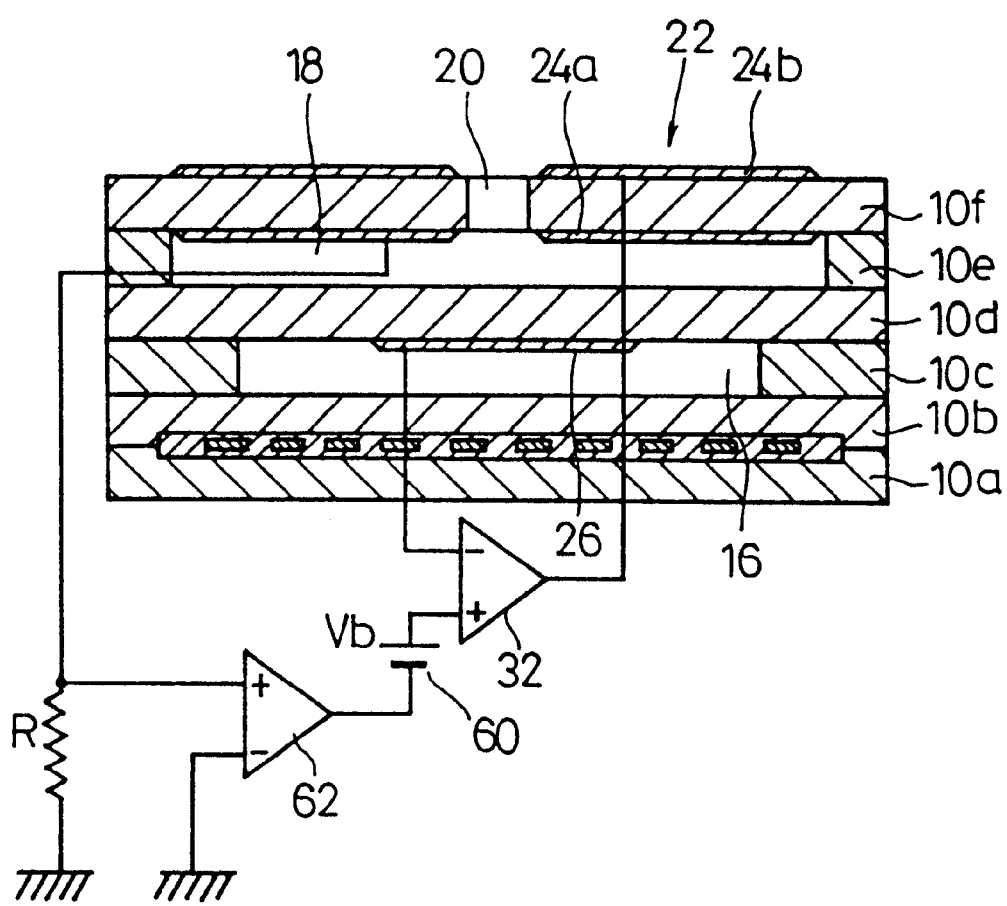
FIG. 5 shows a specified arrangement of a second illustrative embodiment in which the gas sensor according to the present invention is applied to a gas sensor for measuring oxides such as NO, $NO_2$, $SO_2$, $CO_2$, and $H_2O$ contained in, for example, atmospheric air and exhaust gas discharged from vehicles or automobiles, and inflammable gases such as CO and CnHm (hereinafter simply referred to as "gas sensor according to the second embodiment").

Next, a gas sensor according to the second embodiment will be explained with reference to FIG. 5. Components or parts corresponding to those shown in FIG. 1 are designated by the same reference numerals.

The gas sensor according to the second embodiment has approximately the same arrangement as that of the gas sensor according to the first embodiment. However, the former is different from the latter in that the gas sensor according to the second embodiment further comprises a resistor R connected between the inner pumping electrode 24a and GND, and a differential amplifier 62 inserted and connected between one end of the resistor R and a generating source (power source 60) of the reference voltage Vb. Specifically, the one end of the resistor R is connected to a non-inverting terminal of the differential amplifier 62, and an inverting terminal of the differential amplifier 62 is connected to the ground. An output terminal of the differential amplifier 62 is connected to a negative pole of the power source 60.

The gas sensor according to the second embodiment is wired and connected such that the current, which flows between the inner pumping electrode 24a and the outer pumping electrode 24b corresponding to the oxygen pumped out by the oxygen pump 22, is converted into a voltage corresponding to a value of the current in accordance with the voltage drop in the resistor R, and the voltage is applied to the non-inverting terminal of the differential amplifier 62.

In general, the current flows through the oxygen pump 22 when the oxygen is pumped out by the oxygen pump 22. Therefore, the amount corresponding to the voltage drop resulting from the impedance of the oxygen pump 22 appears as an error in the operation of level adjustment for the pumping voltage Vp.

However, in the gas sensor according to the second embodiment, the current flowing through the oxygen pump 22 is converted into the voltage by using the resistor R, and the voltage is amplified by the differential amplifier 62 with a predetermined gain to obtain a voltage which is superimposed on the power source 60. Namely, only the amount corresponding to the voltage drop resulting from a boundary resistance (impedance) of the inner pumping electrode 24a is superimposed on the voltage between the inner pumping electrode 24a and the reference electrode 26. The amount corresponding to the voltage drop is considerably decreased. Therefore, it is sufficient for the amount corresponding to the voltage drop to be slightly corrected, and hence the accuracy is improved to that extent. In other words, the amount corresponding to the voltage drop resulting from the impedance of the oxygen pump 22 is reflected in the reference voltage Vb (or superimposed on the reference voltage Vb). Accordingly, it is possible to effectively absorb the error resulting from the impedance of the oxygen pump 22 with respect to the pumping voltage Vp, making it possible to perform the feedback control for the pumping voltage Vp with a high degree of accuracy. This results in highly accurate detection of the oxygen concentration in the gas-introducing space 18.

The gas sensor according to the second embodiment has an effect that the occurrence of oscillation is suppressed in the feedback control system for controlling the pumping voltage Vp to be supplied to the oxygen pump 22 so that the oxygen concentration in the gas-introducing space 18 is a predetermined concentration, in the same manner as the gas sensor according to the first embodiment. Namely, the two objects, i.e., the suppression of oscillation and the improvement in accuracy can be achieved only by using the gas sensor according to the second embodiment. Moreover, a large effect is also obtained in that the combined structure for achieving the two objects is extremely simple.

The improvement in characteristics achieved by the gas sensor according to the second embodiment (working example) will be explained, while comparing it with the conventional gas sensor (comparative example).

At first, FIG. 6 shows a table for comparing actual amounts corresponding to the electromotive force obtained in the comparative example with those obtained in the working example, in which it is intended to correct and control the amount corresponding to the electromotive force to be 400 mV when the oxygen concentration in the measurement gas is changed. In the comparative example, the amount corresponding to the electromotive force is greatly decreased when the oxygen concentration is high. On the contrary, the degree of the decrease is greatly improved in the working example, although the decrease slightly occurs.

Figure 7:
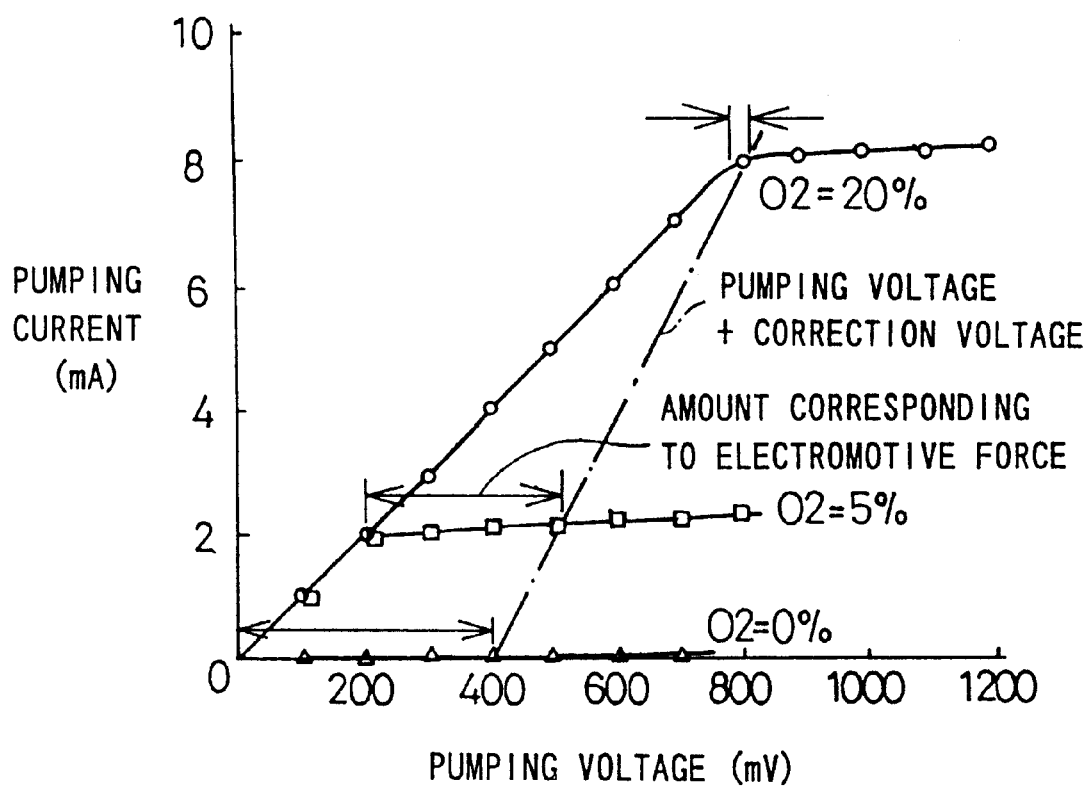
FIG. 7 shows a limiting current characteristic of the gas sensor concerning the comparative example.
Figure 8:
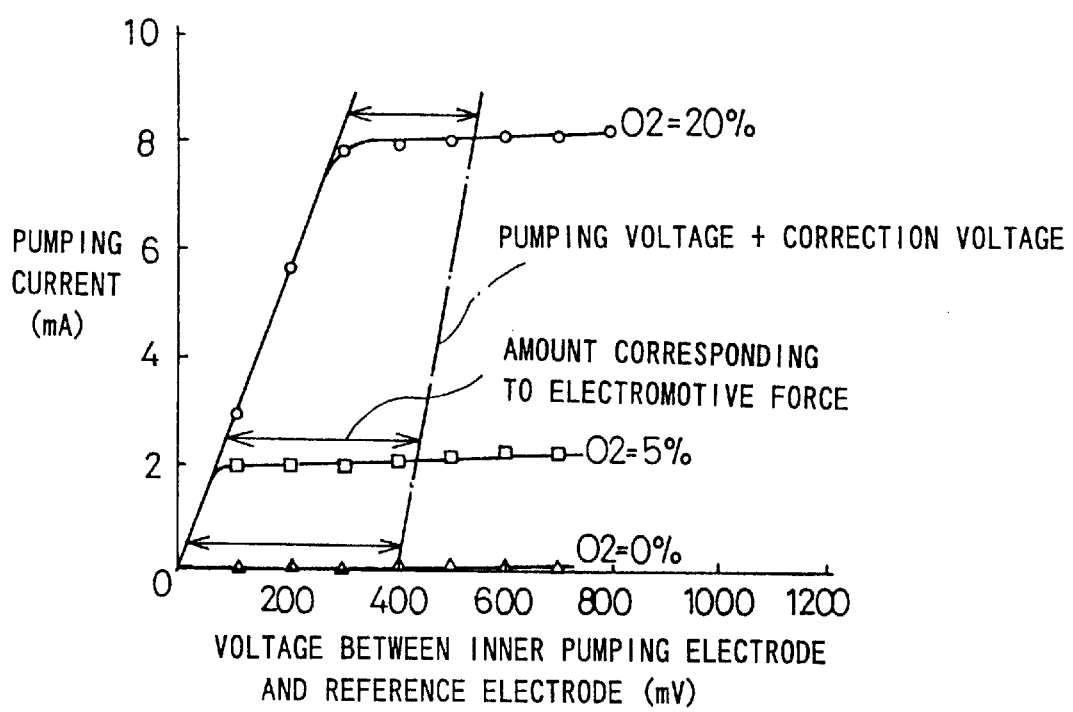
FIG. 8 shows a limiting current characteristic of the gas sensor concerning the working example.

FIGS. 7 and 8 show such situations as described above. In this comparative test, the temperature of the gas sensor is adjusted so that the impedance of the oxygen pump 22 is 100Ω in any case.

In the comparative example (Japanese Utility Model Publication No. 7-45004), the correction voltage is ideally (100Ω×pumping current) because the impedance of the oxygen pump 22 is 100Ω. However, in fact, correction is successful for only (50Ω×pumping current) which is ½ of (100Ω×pumping current). Such unsuccessful correction is caused by oscillation. In a range of not less than (50Ω× pumping current), the control system suffers an oscillation phenomenon, making it impossible to perform control.

In the comparative example, in order to measure the impedance of the oxygen pump 22, an amount corresponding to an alternating current (500 to 100 kHz) is superimposed on the power source so that the impedance of the oxygen pump is measured by using the alternating current voltage. However, oscillation tends to occur because the amount corresponding to the alternating current is subjected to positive feedback. For this reason, the output of the operational amplifier is subjected to positive feedback by the aid of a low pass filter so that the amount corresponding to the alternating current is eliminated. Thus only an amount corresponding to a direct current (for correcting voltage drop) is subjected to positive feedback, and an amount of voltage drop is superimposed on the pumping voltage Vp. In the experiment, the alternating current has a frequency of 10 kHz, and the low pass filter has a cut-off frequency of 1 kHz. In this system, the heater is not controlled on the basis of a signal of the amount corresponding to the alternating current.

According to the experiment, the oscillation phenomenon caused by the direct current component occurs at an extremely low frequency of not more than 50 Hz. Therefore, the oscillation still tends to occur due to the amount corresponding to the direct current in the case of the low pass filter which makes cutting for those having a frequency of not less than several hundreds Hz.

On the other hand, in the working example, when the oxygen pump 22 has an impedance of 100 Ω, the impedance between the inner pumping electrode 24a and the reference electrode 26 is 35Ω, and an ideal value of the correction voltage is (35Ω×pumping current). However, in the same manner as the comparative example, correction is actually successful for (17.5Ω×pumping current) which is ½ of (35Ω×pumping current).

However, as clarified from the characteristic shown in FIG. 8 and the table shown in FIG. 6, when the oxygen concentration is increased, the effect of correction is greatly improved in the working example as compared with the comparative example. This is based on the effect that the amount of correction is greatly decreased in the correction performed in the working example as compared with the comparative example. The decreasing effect is much greater than an expected effect (since only the inner pumping electrode 24a of the oxygen pump 22 is utilized, the expected effect is ½ of that in the comparative example in which the outer pumping electrode 24b is also used).

This is because of the following reason. Namely, in the case of the comparative example, it is necessary to correct all of the impedance Zp of the oxygen pump 22. On the contrary, in the case of the working example, Z1, Z2, and Z3 in the following expression can be neglected.

$Zp=Z1+Z2+Z3+Z4$

Z1: boundary resistance between the outer pumping electrode 24 and the second solid electrolyte layer 10f;

Z2: boundary resistance between $ZrO_2$ grains in the second solid electrolyte layer 10f;

Z3: $ZrO_2$ grain resistance in the second solid electrolyte layer 10f;

Z4: boundary resistance between the inner pumping electrode 24a and the second solid electrolyte layer 10f.

In general, in the case of the oxygen pump 22 provided with the heater 12, the outer pumping electrode 24a has a lower temperature than the inner pumping electrode 24a. Therefore, the outer pumping electrode 24b tends to have a higher boundary resistance. However, in the working example, it is possible to neglect the outer pumping electrode 24b having the lower temperature. Accordingly, the effect to decrease the correction voltage, which exceeds those expected, can be obtained. Thus it is possible to enhance the accuracy, for example, even when a means for measuring the impedance, a means for controlling the heater based thereon, and a means for controlling the correction voltage are not used.

The increase in impedance of the oxygen pump 22 during the course of use is principally caused by the increase in boundary resistance of the outer pumping electrode 24b. According to the working example, correction is performed while neglecting the outer pumping electrode 24b. Therefore, it is possible to sufficiently respond to the increase in impedance during the course of use.

Figure 9:
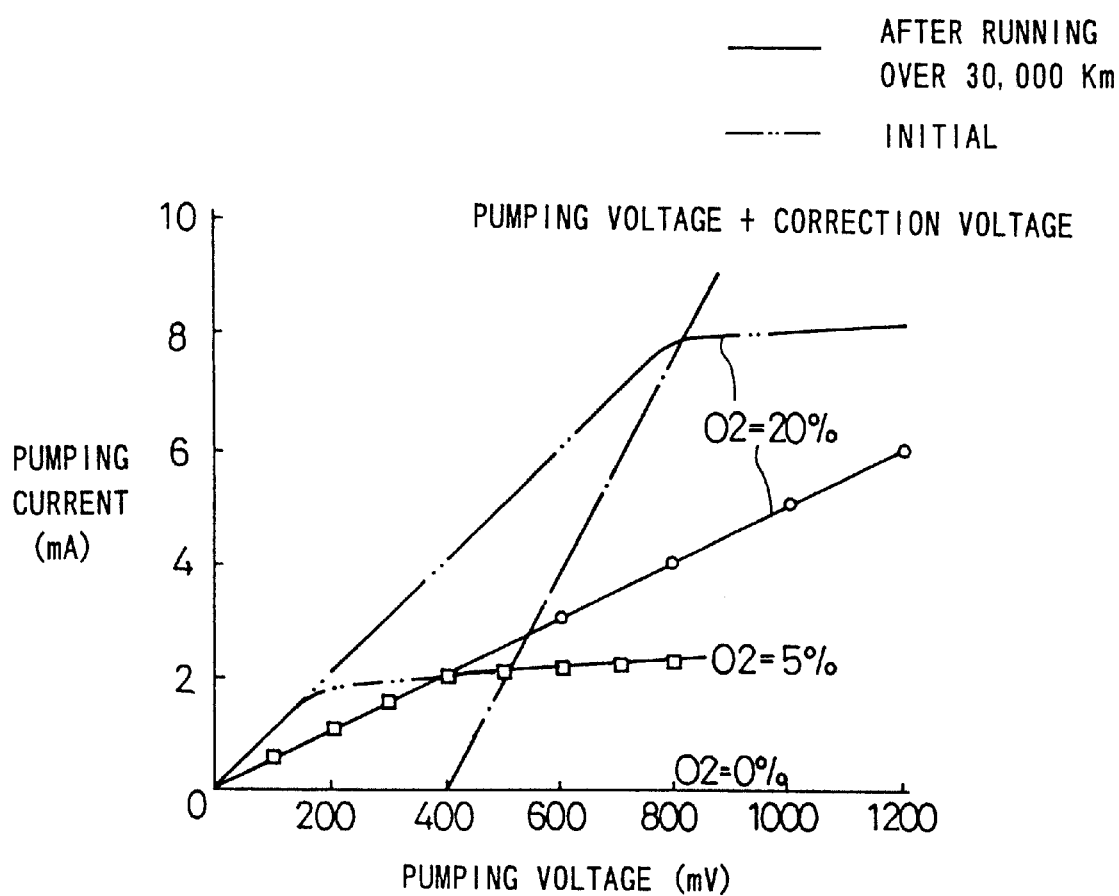
FIG. 9 shows a limiting current characteristic of the gas sensor concerning the comparative example, illustrating a state of correction after test car running over 30,000 km by using a test car having a 2.0 L in-line 4-cylinder engine.
Figure 10:
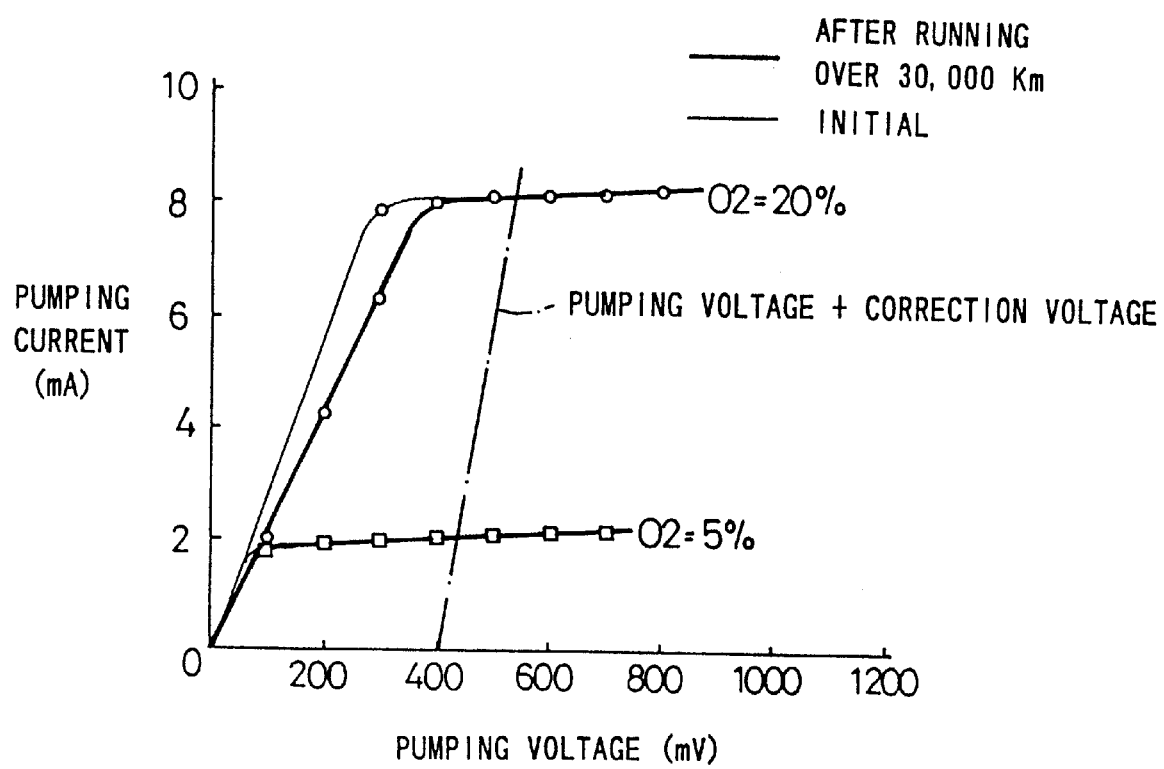
FIG. 10 shows a limiting current characteristic of the gas sensor concerning the working example, illustrating a state of correction after test car running over 30,000 km by using a test car having a 2.0 L in-line 4-cylinder engine.

FIGS. 9 and 10 illustrate states of correction after test car running over 30,000 km by using a test car having a 2.0 L in-line 4-cylinder engine respectively. In FIG. 9, a two-dot chain line indicates a characteristic obtained at a stage of running start-up (initial stage), and a solid line indicates a characteristic obtained after running over 30,000 km. In FIG. 10, a thin solid line indicates a characteristic obtained at a stage of running start-up (initial stage), and a thick solid line indicates a characteristic obtained after running over 30,000 km.

As shown in FIG. 9, in the case of the comparative example, no correction can be effected at all at a concentration of oxygen of 20%, and the operation point at the flat portion barely appears at a concentration of 5%. On the contrary, as shown in FIG. 10, in the case of the working example, the operation can be still performed at the flat portion even when the oxygen concentration is 20%. Therefore, it is understood that the gas sensor concerning the working example, i.e., the gas sensor according to the second embodiment is useful to perform the correction.

Next, a modified embodiment of the gas sensor according to the second embodiment will be explained with reference to FIG. 11. Components or parts corresponding to those shown in FIG. 4 are designated by the same reference numerals, duplicate explanation of which will be omitted.

Figure 11:
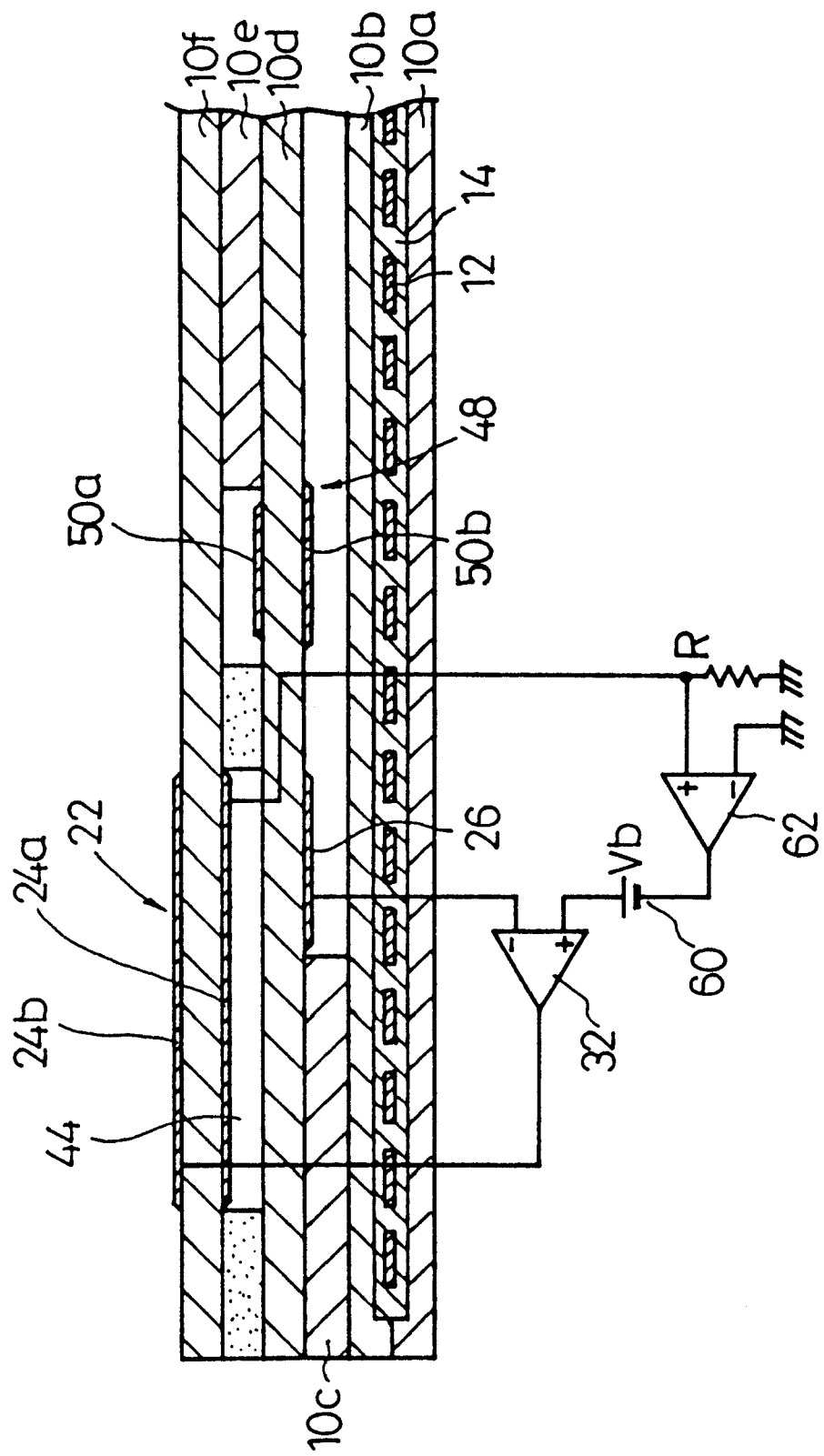
FIG. 11 shows a specified arrangement of a modified embodiment of the gas sensor according to the second embodiment.
Figure 13:
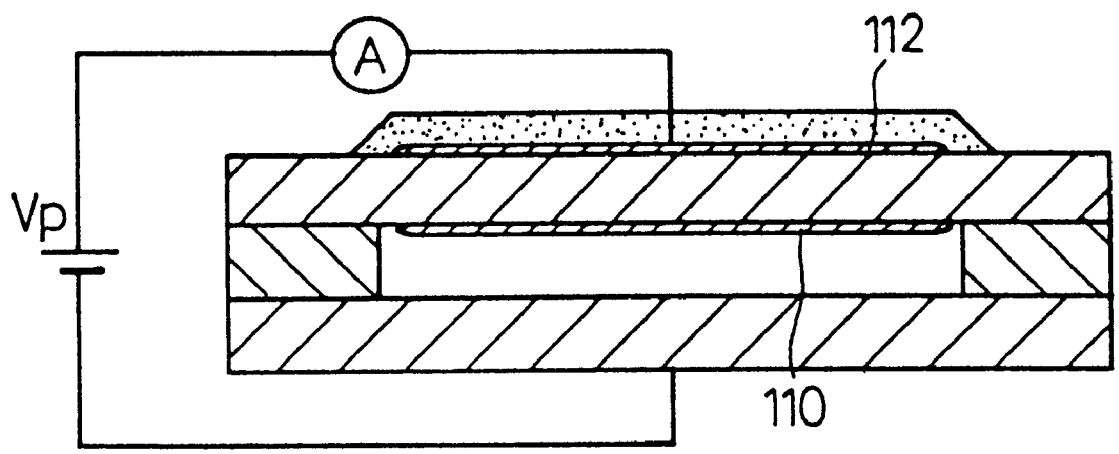
FIG. 13 shows an arrangement illustrating a limiting current type oxygen sensor (No. 1) based on the use of the conventional oxygen pump.
Figure 15:
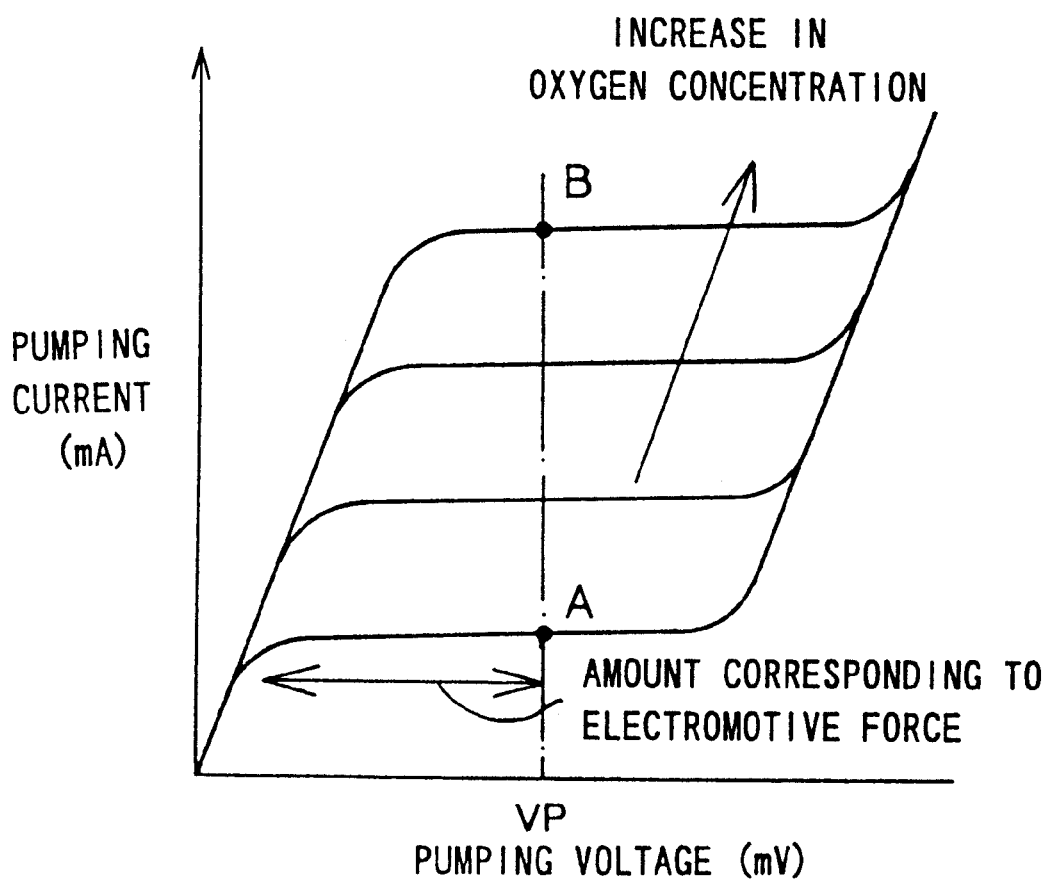
FIG. 15 shows a limiting current characteristic of the limiting current type oxygen sensor based on the use of the conventional oxygen pump.
Figure 16:
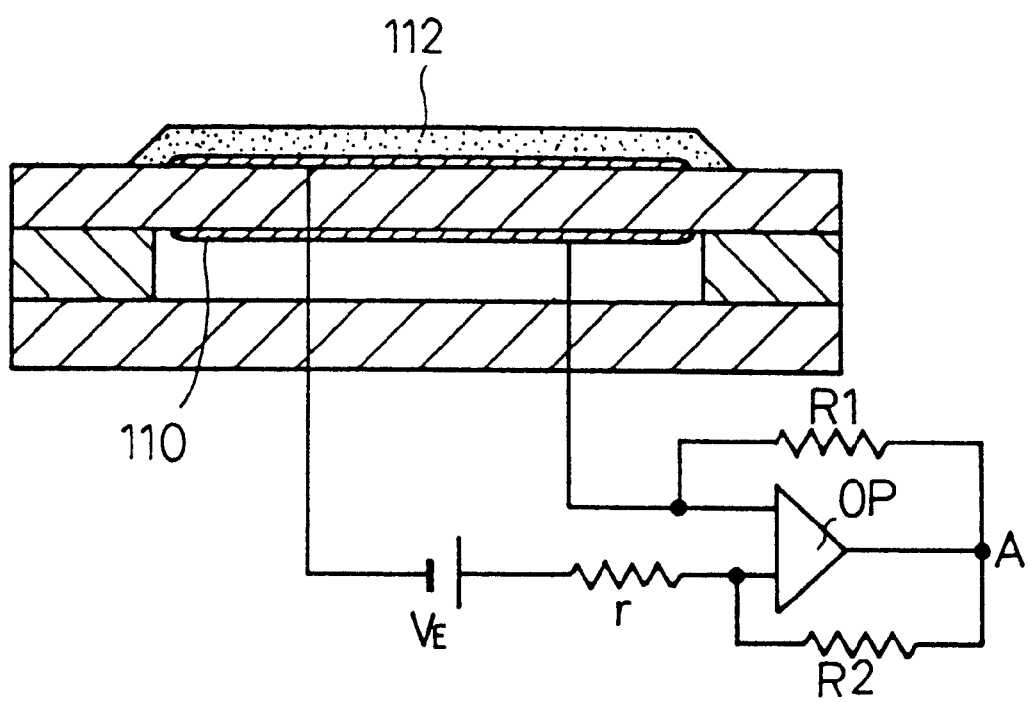
FIG. 16 shows an arrangement illustrating another conventional gas sensor.
Figure 17:
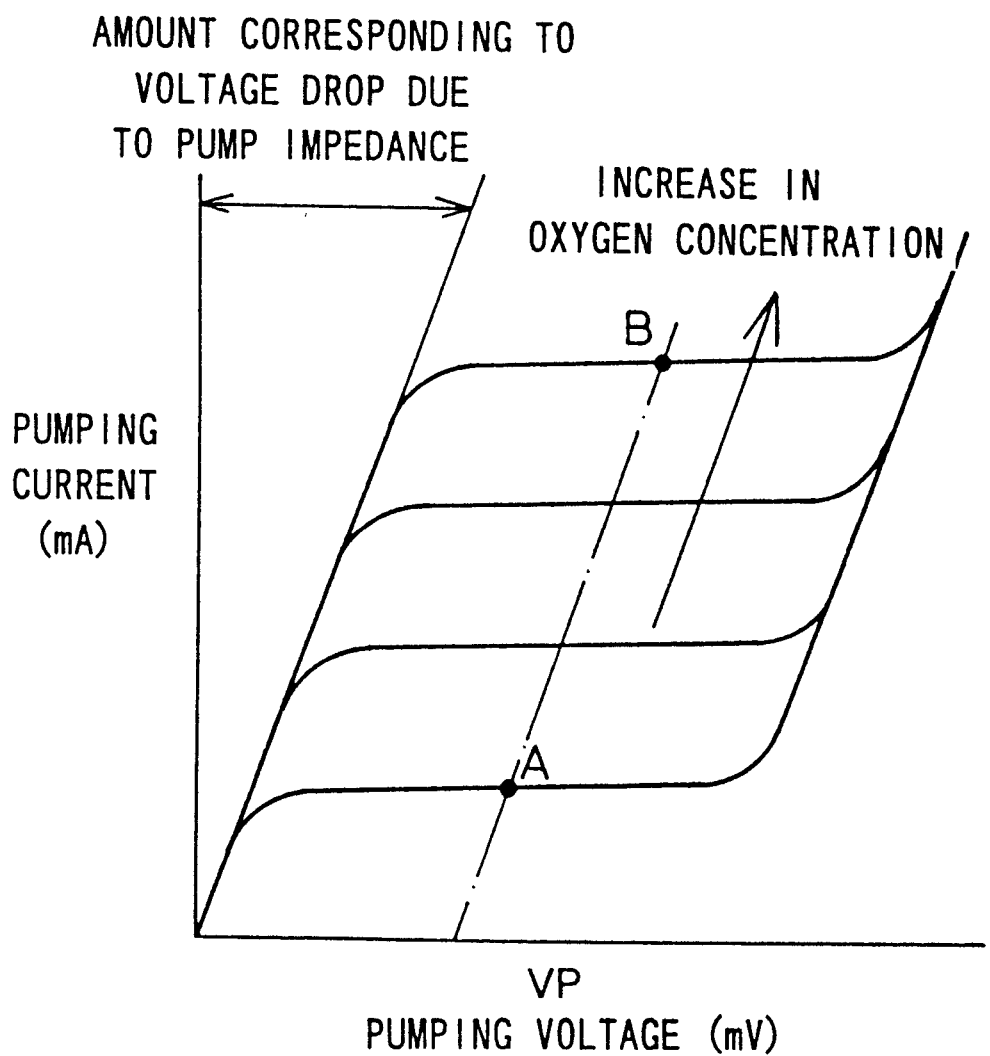
FIG. 17 shows a limiting current characteristic of a gas pump concerning the another conventional gas sensor.

As shown in FIG. 11, the gas sensor according to this modified embodiment is constructed in approximately the same manner as the gas sensor according to the modified embodiment of the first embodiment. However, the former is different from the latter in that a resistor R is connected between the inner pumping electrode 24a and GND, and a differential amplifier (operational amplifier) 62 is inserted and connected between one end of the resistor R and a generating source (power source 60) of the reference voltage Vb. Specifically, the one end of the resistor R is connected to a non-inverting terminal of the differential amplifier 62, and an inverting terminal of the differential amplifier 62 is connected to the ground. An output terminal of the differential amplifier 62 is connected to a negative pole of the power source 60.

The gas sensor according to this modified embodiment also functions in the same manner as the gas sensor according to the second embodiment. Namely, the current flowing through the oxygen pump 22 is converted into a voltage by using the resistor R, and the voltage is amplified by the differential amplifier 62 with a predetermined gain to obtain an amplified voltage which is superimposed on the power source 60. Accordingly, it is possible to effectively absorb the error resulting from the impedance of the oxygen pump 22 with respect to the pumping voltage Vp, making it possible to perform the feedback control for the pumping voltage Vp with a high degree of accuracy.

It is a matter of course that this invention is not limited to the embodiments described above, which can be constructed in other various forms without deviating from the gist or essential characteristics of this invention.

What is claimed is:

1. A gas sensor comprising:

a first space surrounded by first, second and third substrates composed of solid electrolytes, for introducing a measurement gas thereinto;

a gas-pumping means including inner and outer electrodes formed inside and outside said first space surrounded by said first, second and third substrates, respectively, said third substrate interposed between both said electrodes, and a pumping power source for applying, between said both electrodes, a control voltage for pumping out a predetermined gas component;

a second space surrounded by substrates composed of solid electrolytes, for introducing a reference gas thereinto;

a measuring means for measuring a terminal voltage between a reference electrode formed on said first substrate and disposed on a side of said second space and said inner electrode of said gas-pumping means; and a control voltage-adjusting means for adjusting a level of said control voltage on the basis of said terminal voltage.

2. The gas sensor according to claim 1, wherein said control voltage-adjusting means is provided with a comparing means for determining a deviation between (a) the terminal voltage between the reference electrode and the inner pumping electrode and (b) a comparative voltage, and said level of said control voltage is adjustable on the basis of said deviation obtained by said comparing means.

3. The gas sensor according to claim 2, wherein said gas sensor further comprises:

a current-detecting means for detecting a current flowing through said gas-pumping means when said gas component is pumped out by said gas-pumping means; and a comparative voltage-adjusting means for adjusting said level of said comparative voltage on the basis of a value of said current detected by said current-detecting means.

4. The gas sensor according to claim 1, wherein a gas diffusion rate-determining section for giving a predetermined diffusion resistance to said measurement gas is provided at a passage for introducing said measurement gas into said first space.

5. The gas sensor according to claim 4, further comprising:

a third space for introducing said measurement gas in said first space thereinto;

a second gas diffusion-rate determining section provided at a passage for introducing said measurement gas into said third space, for giving a predetermined diffusion resistance to said measurement gas;

a measurement gas-decomposing means disposed in said third space, for decomposing and degrading said predetermined gas component in said measurement gas; and a gas component-detecting means for detecting said predetermined gas component decomposed and degraded by said measurement gas-decomposing means.

6. The gas sensor according to claim 4, further comprising:

a third space for introducing said measurement gas in said first space thereinto;

a second gas diffusion-rate determining section provided at a passage for introducing said measurement gas into said third space, for giving a predetermined diffusion resistance to said measurement gas;

a gas component supply means for feeding said predetermined gas component to said third space; and a gas component-detecting means for detecting said gas component fed by said gas component supply means.

7. A method for controlling a gas sensor, said gas sensor comprising:

a first space surrounded by first, second and third substrates composed of solid electrolytes, for introducing a measurement gas thereinto;

a gas-pumping means including inner and outer electrodes formed inside and outside said first space surrounded by said first, second and third substrates respectively, said third substrate interposed between both said electrodes, and a pumping power source for applying, between said both electrodes, a control voltage for pumping out a predetermined gas component;

a second space surrounded by substrates composed of solid electrolytes, for introducing a reference gas thereinto; and a reference electrode formed on said first substrate and disposed on a side of said second space;

said method comprising the steps of measuring a terminal voltage between said reference electrode and said inner electrode of said gas-pumping means, and adjusting a level of said control voltage on the basis of said terminal voltage.

8. The method according to claim 7, wherein said control voltage is adjusted by determining a deviation between said terminal voltage and a comparative voltage, and adjusting said level of said control voltage on the basis of said obtained deviation.

9. The method according to claim 7, wherein a current flowing through said gas-pumping means is detected when said gas component is pumped out by said gas-pumping means, and a level of said comparative voltage is adjusted on the basis of a value of said detected current.

10. The method according to claim 7, wherein said gas sensor further comprises a gas diffusion rate-determining section for giving a predetermined diffusion resistance to said measurement gas, provided at a passage for introducing said measurement gas into said first space.

11. The method according to claim 10, wherein said gas sensor further comprises:
   a third space for introducing said measurement gas in said first space thereinto;
   a second gas diffusion-rate determining section provided at a passage for introducing said measurement gas into said third space, for giving a predetermined diffusion resistance to said measurement gas;
   a measurement gas-decomposing means disposed in said third space, for decomposing and degrading said predetermined gas component in said measurement gas; and
   a gas component-detecting means for detecting said predetermined gas component decomposed and degraded by said measurement gas-decomposing means.

12. The method according to claim 10, wherein said gas sensor further comprises:
   a third space for introducing said measurement gas in said first space thereinto;
   a second gas diffusion-rate determining section provided at a passage for introducing said measurement gas into said third space, for giving a predetermined diffusion resistance to said measurement gas;
   a gas component supply means for feeding said predetermined gas component to said third space; and
   a gas component-detecting means for detecting said gas component fed by said gas component supply means.

13. A gas concentration controller comprising:
   a first space surrounded by first, second and third substrates composed of solid electrolytes, for introducing a measurement gas thereinto;
   a gas diffusion rate-determining section provided at a passage for introducing said measurement gas into said first space, for giving a predetermined diffusion resistance to said measurement gas;
   a gas-pumping means including inner and outer electrodes formed inside and outside said first space surrounded by said substrates respectively, said third substrate interposed between both said electrodes, and a pumping power source for applying, between said both electrodes, a control voltage for pumping out a predetermined gas component;
   a second space surrounded by substrates composed of solid electrolytes, for introducing a reference gas thereinto;
   a measuring means for measuring a terminal voltage between a reference electrode formed on said first substrate and disposed on a side of said second space and said inner electrode of said gas-pumping means; and
   a control voltage-adjusting means for adjusting a level of said control voltage on the basis of said terminal voltage.

14. The gas concentration controller according to claim 13, wherein said control voltage-adjusting means is provided with a comparing means for determining a deviation between said terminal voltage and a comparative voltage, and said level of said control voltage is adjusted on the basis of said deviation obtained by said comparing means.

15. The gas concentration controller according to claim 13, further comprising:
   a current-detecting means for detecting a current flowing through said gas-pumping means when said gas component is pumped out by said gas-pumping means; and
   a comparative voltage-adjusting means for adjusting a level of said comparative voltage on the basis of a value of said current detected by said current-detecting means.

16. A method for controlling gas concentration, comprising the steps of:
   introducing a measurement gas into a first space surrounded by first, second and third substrates composed of solid electrolytes;
   applying a control voltage for pumping out a predetermined gas component between inner and outer electrodes formed inside and outside said first space surrounded by said substrates respectively, said third substrate interposed between said inner and outer electrodes;
   introducing a reference gas into a second space surrounded by substrates composed of solid electrolytes;
   measuring a terminal voltage between a reference electrode formed on said first substrate and disposed on a side of said second space and said inner electrode; and
   adjusting a level of said control voltage on the basis of said terminal voltage.

17. The method according to claim 16, wherein said control voltage is adjusted by determining a deviation between said terminal voltage and a comparative voltage, and adjusting said level of said control voltage on the basis of said obtained deviation.

18. The method according to claim 16, wherein a current flowing through said third substrate is detected when said predetermined gas component is pumped out, and a level of said comparative voltage is adjusted on the basis of a value of said detected current.

19. The method according to claim 16, wherein a predetermined diffusion resistance is given to said measurement gas when said measurement gas is introduced into said first space.

* * * * *